United States Patent
Berens

(10) Patent No.: US 7,465,838 B2
(45) Date of Patent: Dec. 16, 2008

(54) CHIRAL DIOLS, THEIR MANUFACTURE AND LIGANDS AND CATALYSTS DERIVED THEREFROM

(75) Inventor: Ulrich Berens, Binzen (DE)

(73) Assignee: Ciba Specialty Chemical Corp., Tarrytown, NY (US)

( * ) Notice: Subject to any disclaimer, the term of this patent is extended or adjusted under 35 U.S.C. 154(b) by 690 days.

(21) Appl. No.: 10/528,510

(22) PCT Filed: Sep. 23, 2003

(86) PCT No.: PCT/EP03/10568

§ 371 (c)(1),
(2), (4) Date: Mar. 18, 2005

(87) PCT Pub. No.: WO2004/031109

PCT Pub. Date: Apr. 15, 2004

(65) Prior Publication Data

US 2006/0030737 A1 Feb. 9, 2006

(30) Foreign Application Priority Data

Oct. 1, 2002 (EP) ................................. 02405847

(51) Int. Cl.
*C07C 33/26* (2006.01)
(52) U.S. Cl. .................. 568/811; 568/715; 568/807; 568/808; 568/9; 568/12; 568/17
(58) Field of Classification Search ................ 568/811, 568/715, 807, 808, 9, 12, 17
See application file for complete search history.

(56) References Cited

OTHER PUBLICATIONS

Ramachandran et al., Tetrahedron Letters, 38(14), 1997, pp. 2417-2420; abstract only.*
Brown et al., Tetrahedron Letters, 37(22), 1996, pp. 3795-3798; abstract only.*
G. Kraus et al., J. Org. Chem., vol. 60, (1995), pp. 1154-1159.
G. Kraus et al., J. Am. Chem. Soc., vol. 115, (1993), pp. 5859-5860.
F. Kaiser et al., J. Org. Chem., vol. 67, (2002), pp. 9248-9256.
M. F. Semmelhack et al., Tetrahedron Letters, vol. 25, No. 30, pp. 3171-3174, (1984).
M. Saulnier et al., Tetrahedron Letters, vol. 24, No. 49, pp. 5435-5438, (1983).
G. Kraus et al., Synlett, Jul. 1993, pp. 525-526.
N. Meyer et al., Chem. Ber., vol. 113, pp. 1304-1319, (1980).
R. Butz et al., J. Org. Chem., vol. 67, pp. 2699-2701, (2002).
H. Kleijn et al., Tetrahedron Letters, vol. 42, (2001), pp. 3933-3937.
P. Skabara et al., J. Org. Chem., vol. 64, (1999), pp. 6418-6424.
P. Ramachandran et al., Tetrahedron Letters, vol. 38, No. 14, pp. 2417-2420, (1997).
A. Deron et al., Heteroatom Chemistry, vol. 13, No. 2, (2002), pp. 157-164.
S. Fujii et al., Journal of Fluorine Chemistry, vol. 30, (1986), pp. 415-428.
I. Tikk et al., J. Chem. Research (S), (1987), p. 95.
Database Crossfire Beilstein Accession No. 1284577.
B. Jousseaume et al., Tetrahedron, vol. 45, No. 4, pp. 1145-1154, (1989).

* cited by examiner

*Primary Examiner*—Elvis O Price
(74) *Attorney, Agent, or Firm*—Mervin G. Wood

(57) ABSTRACT

The present invention relates to a method for the preparation of $C_2$-symmetric 1,4-diols of the formula IVA or IVB, wherein ring A, $R_1$ and $R_2$ have the meanings given in the specification, that makes use of the metallation of pure enantiomers of α-(aryl or heteroaryl)-α-substituted alkanol compounds or the use of said alkanol compounds in the preparation of said mmetric 1,4-diols; novel $C_2$-symmetric 1,4-diols in enantiomerically pure form; and methods of use or their use in the synthesis of chiral ligands which find use to produce catalysts for a variety of asymmetric transformations such as hydrogenations.

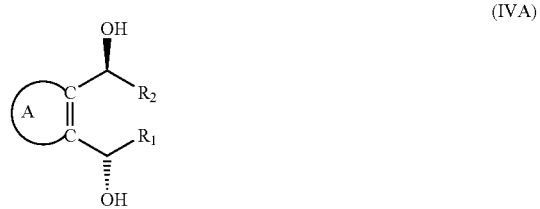

(IVA)

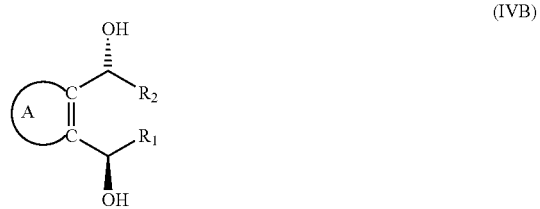

(IVB)

13 Claims, No Drawings

CHIRAL DIOLS, THEIR MANUFACTURE AND LIGANDS AND CATALYSTS DERIVED THEREFROM

This application is the national stage application of PCT/EP 03/10568, filed Sep. 23, 2003, which is herein incorporated by reference.

FIELD OF THE INVENTION

The present invention relates to a method for the preparation of $C_2$-symmetric 1,4-diols that makes use of the metallation of pure enantiomers of α-(aryl or heteroaryl)-α-substituted alkanol compounds or the use of said alkanol compounds in the preparation of $C_2$-symmetric 1,4-diols; novel $C_2$-symmetric 1,4-diols in enantiomerically pure form; and methods of use or their use in the synthesis of chiral ligands which find use to produce catalysts for a variety of asymmetric transformations such as hydrogenations, allylations or alkylations.

BACKGROUND OF THE INVENTION

Chiral enatiomerically pure 1,4-diols of type A (see Scheme I below; R=organic moieties) have been utilized in the synthesis of ligands, with the DuPHOS- and BPE-ligands constituting a particular well known example (Burk, M. J. *J. Amer. Chem. Soc.* 1991, 113, 8518). Despite of their relatively simple structure, there are only few methods known for their synthesis. One approach utilises the Kolbe-coupling of enantiomerically pure 3-hydroxy alkanoates (Burk, M. J., Feaster, J. E.; Harlow, R. L.; *Tetrahedron: Asymmetry* 1991, 2, 569). Another approach utilizes the enantioselective reduction of 1,4-diketones (Quallich, G. J., Keavey, K. N., Woodall, T. M. *Tetrahedron Lett.* 1995, 36, 4729), the douple alkylation of enantiopure 1,2-5,6-diepoxy hexane (Machinaga, N., Kibayashi, C. *Tetrahedron Lett.* 1990, 31, 3637), or the multistep functionalisation of carbohydrate derivatives (see for example: Stürmer R., Börner A., Holz J., Voss G. U.S. Pat. No. 6,043,396).

Scheme I:

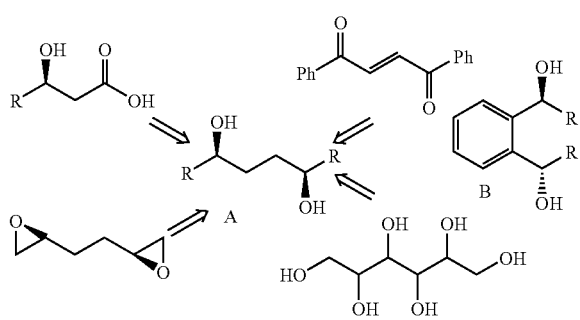

Diols of type B have so far not been used in the synthesis of ligands. An approach for obtaining these diols is provided by the reaction of phthaldialdehyde with an organo-zink reagent (see Scheme II below; Kleijn, H., Jastrzebski, T. B. H., Boersma, J., Koten, G. van *Tetrahedron Lett* 2001, 42, 3933). In the presence of a chiral ligand, the addition stops after the uptake of one equivalent of the organozink reagent to form the hemiacetal 2 with an enantiomeric excess (ee) of up to 80%. When a Grignard reagent is added into the mixture containing 2, a mixture of enantio-enriched chiral diol 3 and meso-diol 4 is formed. The process is attractive insofar that the desired chiral diol 3 can be obtained in a one-pot reaction. However, the starting material 1 is not readily available in large quantities, and the handling of organozink derivatives is difficult and there is only a limited range of these compounds available in commercial quantities. Moreover, diols of type 3 obtained according to this protocol have high ee's up to 85% but are not enantio-pure. Thus, apart from the need to separate 3 from 4, there is also the need to upgrade the ee of 3 to enantiopurity.

Scheme II:

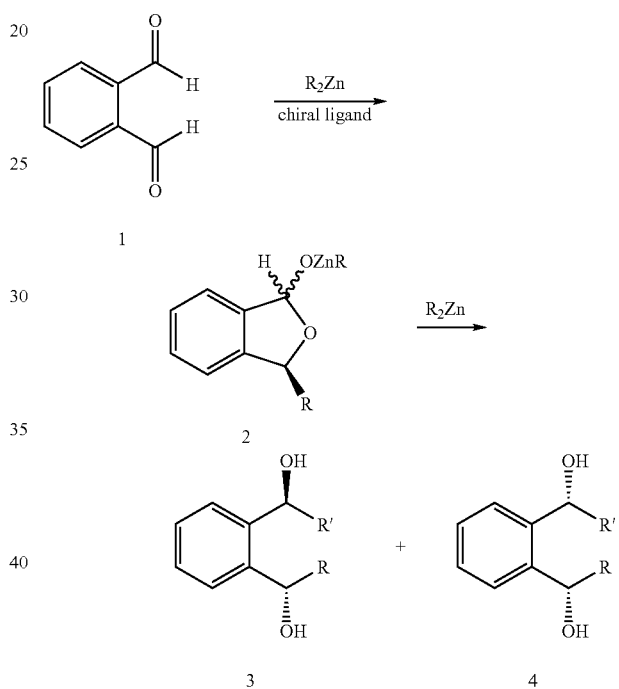

Thus there is a need for novel approaches for the synthesis of $C_2$-symmetric 1,4-diols that allows for obtaining enantiomer pure compounds with a high ee and/or that allow to avoid the disadvantages mentioned above. It is the problem of the present invention to provide a solution manifesting such a novel approach.

Enantiopure 1,4-diols of type A (see for example U.S. Pat. No. 5,021,131) are essential intermediates in the manufacture of chiral ligands such as the BPE-ligands (U.S. Pat. No. 5,008,457) or the DuPHOS-ligands (U.S. Pat. No. 5,171,892). So far, these and related ligands (see EP1082328, U.S. Pat. No. 6,576,772 or WO 03/031456) have been prepared essentially as follows: In the first step the alcohols are activated by a leaving group such as a sulfonate or a cyclic sulfate. In the next step, the activated alcohols are reacted with a phosphine anion where in a nucleophilic $S_N2$ displacement a phosphorus-carbon bond is formed with inversion at the carbon. In order to obtain the phospholane ligand with high optical purity, it is crucial that the optical yield for this displacement is very high.

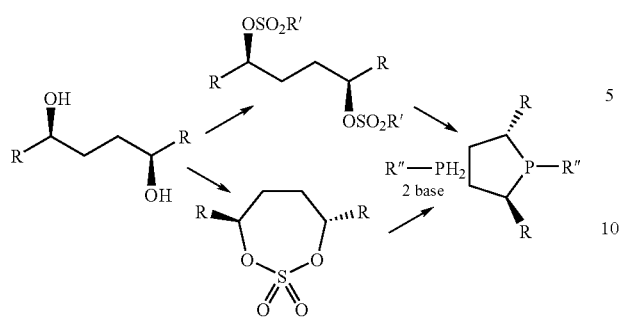

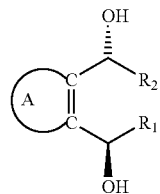

R′ = Me, Aryl

There are numerous examples for clean $S_N2$ displacements of the above type with aliphatic sulfonates or sulfates as leaving group. However, problems arise when the leaving group is in a benzylic position. Both sulfonates or sulfates derived from benzylic alcohols are labile, and the displacement is prone to follow a $S_N1$ pathway with loss of chirality (see *Org. Lett.* 2003, 5, 1273 and references 8a and 8b therein). This is also true for halides as the leaving group, see EP 2 068 526. The present application also provides a solution to overcome these problems.

GENERAL DESCRIPTION OF THE INVENTION

The present invention provides a solution to produce enantiomerically pure diols of type 3 without the need for an ee-upgrading procedure, and also avoids the use of the expensive starting material 1 or organo-zink reagents.

The route starts from enantio-pure α-(aryl or heteroaryl)-alkanols compounds of the formula IA or IB given below which are readily available in commercial quantities, for example via the asymmetric hydrogenation of the corresponding aryl-alkyl ketones with Ru-derived catalysts (Doucet H., Ohkuma T., Murata K., Yokozawa T., Kozawa M., Katayama E., England A. F., Ikariya T., Noyori R. *Angew. Chem., Int. Ed. Engl.* 1998, 37, 1703).

The new principle is to start from the enantio-pure compounds of the formula IA and IB, where surprisingly it has been found that the enantiopurity of the chiral atom present is conserved and at the same time it is possible to obtain the newly introduced chiral atom in pure chiral form under the direction of the chiral atom already present.

Specific Description of the Invention

The invention relates in a first preferred embodiment to a process or method for the preparation of $C_2$-symmetric 1,4-diols of the formula IVA or IVB in high enantiomeric purity,

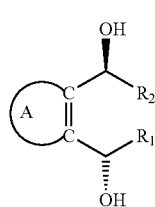
(IVA)

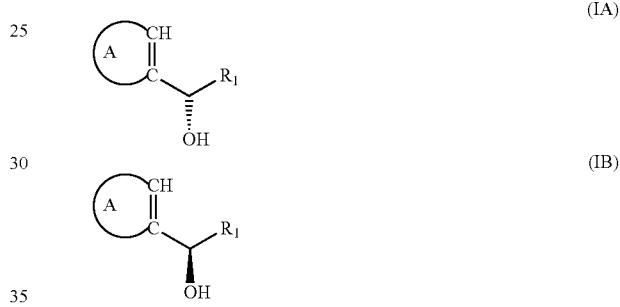

wherein ring A which includes the shown double bond forms a mono-, di- or polycyclic aromatic or heteroaromatic ring and $R_1$ and $R_2$ are, independently of each other, an organic moiety, the process or method comprising reacting an α-(aryl or heteroaryl)-α-substituted alkanol compound of the formula IA (for the synthesis of a compound of the formula IVA) or IB (for the synthesis of a compound of the formula IVB)

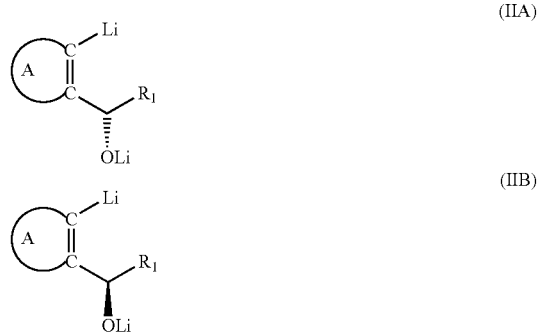

wherein ring A and $R_1$ are as defined under formula IVA and IVB, with a lithiating reagent, optionally in the presence of a tertiary nitrogen base, obtaining an intermediate of the formula IIA (from IA) or IIB (from IB), wherein ring A and $R_1$ have the meanings given under compounds of the formulae IVA and IVB.

These lithiated compounds then allow for two ways of producing the compounds of the formulae IVA or IVB.

In a first preferred variant, the lithiated product of the formula IIA or IIB, respectively, is then reacted with an N,N-di-alkyl-formamide to a hemiacetal compound of the formula IIIA (from IIA) or IIIB (from IIB),

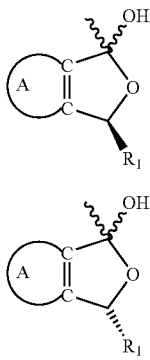

(IIIA)

(IIIB)

wherein ring A, $R_1$ and $R_2$ have the meanings indicated for compounds of the formula IVA and IVB, and subsequently reacted with a Grignard reagent of the formula $R_2MgX$ wherein $R_2$ is an organic moiety and X is halogen (or, alternatively, using corresponding lithium, zinc or other metal comprising compounds that allow for introduction of $R_2$, which may lead to increased selectivity and thus constitutes a preferred alternative) to yield the corresponding compounds of formula IVA (from IIIA) and IVB (from IIIB) given above.

Here and in the following it is to be understood that compounds (IIIA) and (IIIA*), or (IIIB) and (IIIB*), in general are in an equilibrium which obviously can depend on the nature of the compounds, the solvent, the temperature etc. As to compounds (IIIA*) and (IIIB*) see below:

(IIIA')

(IIIB')

Surprisingly, the higher the temperature used for the Grignard reaction, the higher selectivity towards the $C_2$-symmetric diols over the compounds of the formula VA (from IIIA) and VB (from IIIB),

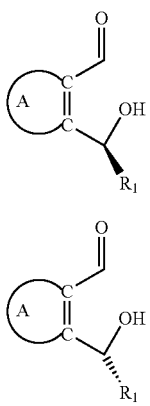

(VA)

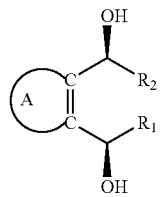

(VB)

wherein ring A, $R_1$ and $R_2$ have the meanings indicated for compounds of the formula IVA and IVB, is formed.

The reaction with the N,N-dialkylformamide takes place in the reaction mixture resulting from the lithiation.

In a second preferred variant, instead of the reaction with the the N,N-dialkylformamide an aldehyde of the formula VI $$R_2\text{—CH}\!\!=\!\!O \quad (VI)$$

wherein $R_2$ is as defined for compounds of the formulae IVA and IVB, is reacted with the intermediate of the formula IIA to yield a compound of the formula IVA (and the meso by-product of the formula VA) or of the formula IIB to yield a compound of the formula IVB (and the meso by-product of the formula VB).

This reaction is very convenient in that it represents a one-pot reaction, still allowing for the use of the easily available starting materials of the formula IA or IB, respectively.

The invention also relates to the novel compounds of the formula IVA and IVB wherein ring A, $R_1$ and $R_2$ are as defined for a compound of the formula IVA or IVB with the proviso that $R_1$ and $R_2$ are not simultaneously methyl or ethyl, preferably not simultaneously alkyl, more preferably not identical. Preferably, the compounds at the formula IVA and IVB have a high enantiomeric purity.

The invention also relates to the use of compounds of the formula IVA or IVB or methods using these compounds in the synthesis of ligands.

One preferred use/method using these compounds of formula IVA or IVB in the manufacture of ligands is where a compound of the formula IVA or VIB, or either a mixture of a compound of the formula IVA and of the formula VA given below; or a mixture of a compound of the formula IVB and of the formula VB given below; or a compound of the formula VA given below or of the formula VB given below; respectively, is reacted with an aryl phosphinic acid halogenide of the formula VII;

$$\text{Ar—P}(\!\!=\!\!O)(Hal)_2 \quad (VII)$$

wherein Ar is aryl, especially phenyl, and Hal is halogen, especially chloro, in the presence of a base resulting in the formation of a phosphonate ester compound of the formula VIIIA (from IVA) or VII IB (from IVB), respectively,

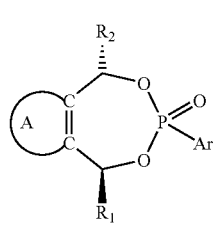

(VIIIA)

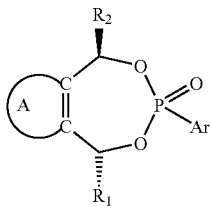
(VIIIB)

wherein ring A, $R_1$ and $R_2$ have the meanings indicated for compounds of the formula IVA and IVB and Ar is aryl, and then reacting a compound of the formula VIIIA or VIIIB with a phosphine of the formula IX or IX*,

$R_3$—$PH_2$ (IX)

$H_2P$—$R_3$*—$PH_2$ (IX*)

(or the corresponding borane adduct of any of these) wherein $R_3$ is a monovalent, $R_3$* a bivalent organic moiety that can be bound to phosphorus, resulting in a phospholane compound of the formula XA or XA* (from VIIIA); or XB or XB* (from VIIIB), respectively,

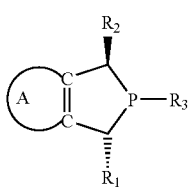
(XA)

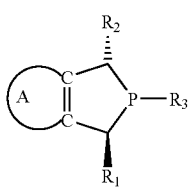
(XB)

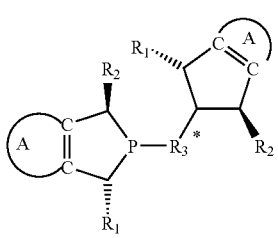
(XA*)

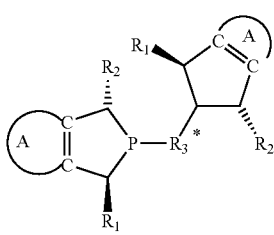
(XB*)

wherein ring A, $R_1$ and $R_2$ have the meanings indicated for compounds of the formula IVA or IVB and $R_3$ or $R_3$* is as defined under formulae IX and IX*, respectively.

Another preferred use/method using these compounds of formula IVA or IVB in the manufacture of ligands is where a compound of the formula IVA or VIB, or either a mixture of a compound of the formula IVA and of the formula VA given below; or a mixture of a compound of the formula IVB and of the formula VB given below; or a compound of the formula VA given below or of the formula VB given below; respectively, is reacted with an aryl phosphinic acid halogenide of the formula VII';

$Ar_2P(=O)Hal$ (VII')

wherein Ar is aryl, especially phenyl, and Hal is halogen, especially chloro, in the presence of a base resulting in the formation of a compound of the formula VIIIA' (from IVA) or VIIIB' (from IVB), respectively,

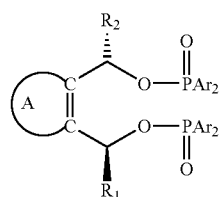
(VIIIA')

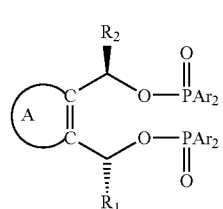
(VIIIB')

wherein ring A, $R_1$ and $R_2$ have the meanings indicated for compounds of the formula IVA and IVB and Ar is aryl, and then reacting a compound of the formula VIIIA' or VIIIB' with a phosphine of the formula IX or IX* (or the corresponding borane adduct thereof) wherein $R_3$ is a monovalent, $R_3$* a bivalent organic moiety that can be bound to phosphorus, resulting in a phospholane compound of the formula XA or XA* (from VIIIA); or XB or XB* (from VIIIB), respectively, wherein ring A, $R_1$ and $R_2$ have the meanings indicated for compounds of the formula IVA or IVB and $R_3$ or $R_3$* is as defined under formulae IX and IX*, respectively.

These are novel ligands. Therefore, the compounds of the formula XA, XA*, XB and XB* also are an embodiment of the invention, as well as their complexes with transition metals. These complexes can find use catalysts for the asymmetric hydrogenation of C=N, C=C or C=O double bonds.

It is worthy to note, that there is little precedence for nucleophilic substitution with inversion of benzylic positions, as found in the reaction leading to compounds of the formula XA or XB, respectively. Thus, it is surprising that the chiral information can be retained almost completely when a leaving group, such as —OP(O)Ar$_2$, is utilized.

Alternatively, it is possible to react compounds of the formula IVA or IVB, preferably obtained and with the substituents as described herein, especially the corresponding preferred compounds, or mixtures of a compound of the formula IVA and VA or of the formula IVB and VB with an agent introducing an acyl protecting group, especially a lower alkanoyl or aroyl group, e.g. a pivaloyl or benzoyl group, such as with an acyl halogenide, e.g. an alkanoyl- or aroyl-halogenide, such as pivaloylchloride or benzoylchoride, preferably in the presence of a tertiary nitrogen base, to obtain the corresponding bis-hydroxy-protected compounds of the formulae IVA* (from IVA), IVB* (from IVB), or mixtures of a compound of the formula IVA* and VA* (from a mixture of a compound of the formula IVA and VA) or of a compound of the formula IVB* and VB* (from a mixture of a compound of the formula IVB and VB).

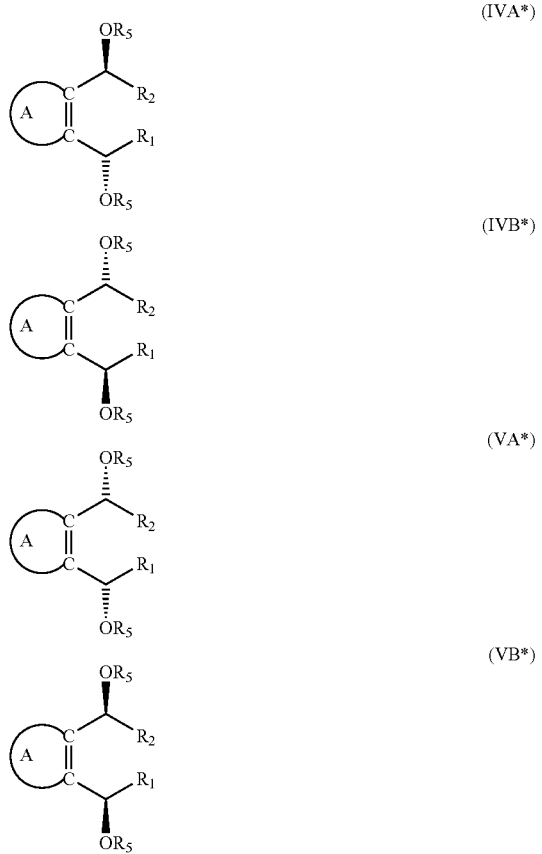

wherein ring A, $R_1$ and $R_2$ have the meanings indicated for compounds of the formula IVA and IVB and $R_5$ is acyl, especially alkanoyl or aroyl, such as pivaloyl or benzoyl.

These compounds, especially those of the formula IVA* or IVB*, can then be reacted to the corresponding compounds of the formulae XA shown above with a compound of the formula IX shown above or a borane adduct thereof, or to a compound of the formula XA* shown above with a compound of the formula IX* shown above or a borane adduct thereof (from IVA*); or of the formula XB shown above with a compound of the formula IX shown above or a borane adduct thereof, or to a compound of the formula XB* shown above with a compound of the formula IX* shown above or a borane adduct thereof (from IVB*); in the case of mixtures of compounds of the formula IVA* and VA* or IVB* and VB* preferably after isolating the compounds of formula IVA* or IVB*, respectively, from the undesired enantiomer of the formula VA* or VB*, respectively, e.g. by chromatography or especially crystallization.

This route offers the advantage that the corresponding acyl derivatives, especially the pivaloyl or benzoyl derivatives, are more easy to crystallize so that the isolation of pure IVA* or pure IVB* is possible in a more convenient way than by chromatography or other separation methods.

Another preferred use/method using the compounds of formula IVA or IVB in the manufacture of ligands is where a compound of the formula IVA or VIB, respectively, is reacted with a compound of the formula XI or XI*, $$R_3\text{—}P(L)_2 \quad \text{(XI)}$$

$$(L)_2\text{—}P\text{—}R_3{}^*\text{—}P\text{-}(L)_2 \quad \text{(XI*)}$$

wherein $R_3$ is a monovalent, $R_3{}^*$ a bivalent organic moiety that can be bound to phosphorus and L is a leaving group, leading to ligands of the formula XIIA or XIIA* (from IVA) and/or XIIB or XIIB* (from IVB),

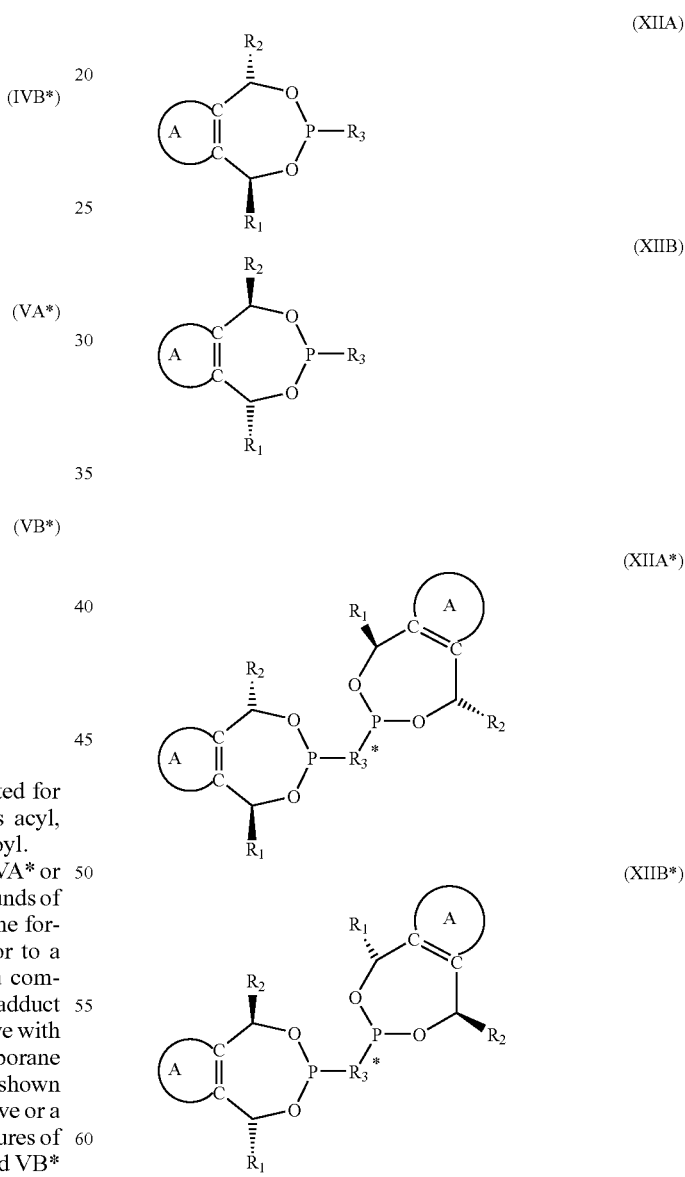

wherein ring A, $R_1$ and $R_2$ have the meanings indicated for compounds of the formula IVA and IVB and $R_3$ is a monovalent, $R_3{}^*$ a bivalent organic moiety that can be bound to phosphorus.

Also these compounds are novel ligands. Therefore, the compounds of the formula XIIA, XIIA*, XIIB and XIIB* also are an embodiment of the invention, as well as their complexes with transition metals. These complexes are especially of use the in 1,4-addition of Grignard compounds in the presence of Cu(I) to α,β-unsaturated carbonyl compounds or (e.g. with Rh, Ru, Ir as transition metals) for hydrogenation reactions, each of these reactions being possible especially in a highly stereoselective way.

As alternative within this second reaction way is where a compound of the formula IVA or VIB, respectively, is reacted with a compound of the formula XI or XI*,

$R_3$—P[N(alk)$_2$]$_2$ (XI**)

[(alk)$_2$N]$_2$P—$R_3$*—P[N(alk)$_2$]$_2$ (XI***)

wherein $R_3$ is a monovalent, $R_3$* a bivalent organic moiety and alk is alkyl which can be linear or cyclic, especially lower alkyl, in particular methyl, ethyl, I-propyl or butyl, or is a heterocyclic radical, under removal of the secondary amine HN(alk$_2$)$_2$, yielding the compound of formula XIIA or XIIA* (from IVA); or XIIB or XIIB* (from IVB) described above, respectively.

An third preferred use/method using the compounds of formula IVA or IVB in the manufacture of ligands is where a compound of the formula IVA or VIB, respectively, is reacted with a compound of the formula XIII,

$R_3R_4$P-L* (XIII)

wherein $R_3$ and $R_4$ are organic moieties that can be bound to phosphorus and L is a leaving group, resulting in a compound of the formula XIVA (from IVA) or XIVB (from IVB), respectively,

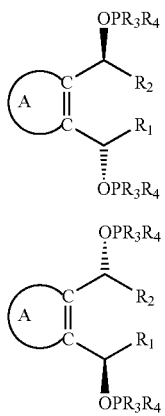

(XIVA)

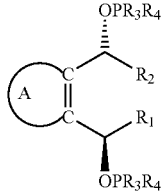

(XIVB)

wherein ring A, $R_1$ and $R_2$ are as defined for compounds of the formula XIVA or XIVB and $R_3$ and $R_4$ each are, independently of the other, an organic moiety that can be bound (stably) to phosphorus.

Also these compounds are novel ligands. Therefore, the compounds of the formula XIVA and XIVB also are an embodiment of the invention, as well as their complexes with transition metals. These complexes are especially of use in hydro-formylation or hydro-cyanation reactions (e.g. with Ni, Rh, Ru, Ir as transition metal), each of these reactions being possible especially in a highly stereoselective way.

As alternative within this third reaction way is where a compound of the formula IVA or VIB, respectively, is reacted with a compound of the formula XIII*,

$R_3R_4$PN(alk)$_2$ (XIII*)

wherein $R_3$ and $R_4$ are, independently from each other, an organic moiety and alk is alkyl which can be linear or cyclic, especially lower alkyl, in particular methyl, ethyl, I-propyl or butyl, or is a heterocyclic radical, under removal of the amine HN(alk)$_2$, yielding the compound if formula XIVA (from IVA) and/or XIVB (from IVB), respectively.

The formation of transition metal complexes of the compounds of the formula XA, XB, XIIA, XIIB, XIVA and/or XIVB can follow methods that are known in the art. They are, for example, obtained by an exchange reaction between the chiral ligands and a complex of the chosen transition metal, in which the bond between metal and ligand must be more labile that the bond that will form between transition metal and phosphorus comprising ligand. Thus, the chiral ligand will replace the original ligand in the coordination to the metal, forming preferred coordination bonds.

The invention relates also to any novel single reaction step that is part of the synthesis of compounds of the formula IVA and/or IVB, as well as of those of formula XA and/or XB, as well as of those of the formula XIIA and/or XIIB, as well as those of the formula XIVA and/or XIVB, or complexes of the ligands of the formulae XA, XB, XIIA, XIIB, XIVA and/or XIV, as well as to any novel intermediate formed during these synthesis steps.

If not indicated otherwise, the symbols and general expressions used above and below preferably have the following meanings:

High enantiomeric purity is preferably an ee of 90 to 100%, especially 95 to 100%. Highly preferred is an ee of 98 to 100%, especially 99 to 100%. An enantiomerically pure form is most preferred.

A mono-, di- or polycyclic aromatic ring A is preferably unsubstituted or substituted arylen (with the two bonds to the rest of the molecule, that is, extending from the double bond forming part of ring A, bound at vicinal C-atoms) wherein aryl is as defined below.

In "unsubstituted or substituted", "substituted", whereever used for a moiety, means that one or more hydrogen atoms in the respective molecule, especially up to 5, more especially up to three, of the hydrogen atoms are replaced by the corresponding number of substituents which preferably are independently selected from the group consisting of alkyl, especially lower alkyl, for example methyl, ethyl or propyl, fluoro, fluoro-lower alkyl, for example trifluoromethyl, $C_6$-$C_{16}$-aryl, especially phenyl or naphthyl (where $C_6$-$C_{16}$-aryl, especially phenyl or napthyl, is unsubstituted or substituted by one or more, especially up to three moieties selected from lower alkoxy, N,N-di-lower alkylamino, N-phenyl-lower alkylamino, N,N-bis(phenyl-lower alkyl)-amino, and fluoro-lower alkyl, e.g. trifluoromethyl), $C_3$-$C_{10}$-cycloalkyl, lower alkoxy, for example methoxy, phenyl-lower alkoxy, N,N-di-lower alkylamino, N-phenyl-lower alkylamino, N,N-bis(phenyl-lower alkyl)-amino and di-lower alkylamino. It goes without saying that substitutents are only at positions where they are chemically possible, the person skilled in the art being able to decide (either experimentally or theoretically) without inappropriate effort which substitutions are possible and which are not.

Aryl (also in arylene) preferably has a ring system of not more than 24 carbon atoms, especially not more than 16 carbon atoms, is preferably mono-, bi- or tric-cyclic, and is unsubstituted or substituted preferably as defined above under "Substituted"; for example, aryl is selected from phenyl, naphthyl, indenyl, azulenyl and anthryl, and is preferably in each case unsubstituted or substituted phenyl or (especially 1- or 2-) naphthyl. Unsubstituted aryl is preferred. Unsubstituted aryl, preferably phenyl, is especially preferred as organic moiety. Aryl as ring A is also ferrocenyl which is one preferred aromatic moiety as ring A in any of the formulae carrying such a ring throughout this application and where the phenyl rings that form part of the ferrocenyl moiety are, in addition to the two bonds extending from the double bond in ring A in formulae IVA, IVB, IVA*, IVB*, IA, IB, IIA, IIB, IIIA, IIIB, VA, VB, VA*, VB*, VIIIA, VIIIB, XA, XB, XA*, XB*, XIIA, XIIB, XIIA*, XIIB*, XIVA and/or XIVB, unsubstituted or substituted, preferably by substituents as described above under "substituted", where preferably the phenyl ring from which the two bonds from ring A extend carries four hydrogen atoms, while the other ring that forms part of the ferrocenyl moiety is identical (including the substituents on the two bonds extending from the double bond shown in the mentioned formulae) or is phenyl that is unsubstituted or substituted by lower alkyl, such as methyl, ethyl and/or isopropyl.

A mono-, di- or polycyclic heteroaromatic ring A is preferably unsubstituted or substituted heteroarylene with heteroaryl as defined below (with the two bonds to the rest of the molecule, that is, extending from the double bond forming part of ring A, bound at vicinal C-atoms).

Heteroaryl is preferably a heterocyclic moiety that is unsaturated in the bonding ring and is preferably a monocyclic or in a broader aspect of the invention bicyclic or tricyclic ring; has 3 to 24, more preferably 4 to 16 ring atoms; wherein at least in the ring bonding to the radical of the molecule of formula I one or more, preferably one to four, especially one or two carbon ring atoms are replaced by a heteroatom selected from the group consisting of nitrogen, oxygen and sulfur, the bonding ring preferably having 4 to 12, especially 5 to 7 ring atoms; heteroaryl being unsubstituted or substituted by one or more, especially 1 to 3, substitutents independently selected from the group consisting of the substituents defined above under "Substituted"; especially being a heteroaryl radical selected from the group consisting of imidazolyl, thienyl, furyl, pyranyl, thiopyranyl, benzofuranyl, benzimidazolyl, pyrazolyl, thiazolyl, oxazolyl, pyridyl, pyrazinyl, pyrimidinyl, isoindolyl, indolyl, indazolyl, triazolyl, isoquinolyl, quinolyl, tetrahydroquinolyl, tetrahydroisoquinolyl, dibenzofuranyl, benzothiophenyl, dibenzothiophenyl, naphthyridinyl, quinoxalyl, quinazolinyl, carbazolyl, β-carbolinyl, phenanthridinyl, acridinyl, perimidinyl, phenanthrolinyl, furazanyl, phenazinyl, phenothiazinyl and phenoxazinyl, each of these radicals being unsubstituted or substituted by one to two radicals selected from the group consisting of fluoro, lower alkyl, especially methyl or tert-butyl, and lower alkoxy, especially methoxy.

An organic moiety $R_1$ or $R_2$ is preferably a moiety that comprises 1 to 50 carbon atoms, that may saturated, unsaturated or partially saturated, wherein carbon atoms may be replaced with heteroatoms, especially selected from N, O, S, Se or P, with the proviso that the moiety is chemically stable. The organic residue may in addition be substituted, or unsubstituted, preferably as described above.

Preferably, such an organic moiety is selected from the group consisting of an unsubstituted or substituted moiety selected from the group consisting of aryl, heterocyclyl, cycloalkyl, aryl-lower alkyl, heterocyclyl-lower alkyl, cycloalkyl-lower alkyl and alkyl.

Aryl preferably is as described above.

Heterocyclyl is preferably a heterocyclic radical that is unsaturated, saturated or partially saturated in the bonding ring and is preferably a monocyclic or in a broader aspect of the invention bicyclic or tricyclic ring; has 3 to 24, more preferably 4 to 16 ring atoms; wherein at least in the ring bonding to the radical of the molecule of formula I one or more, preferably one to four, especially one or two carbon ring atoms are replaced by a heteroatom selected from the group consisting of nitrogen, oxygen and sulfur, the bonding ring preferably having 4 to 12, especially 5 to 7 ring atoms; heteroaryl being unsubstituted or substituted by one or more, especially 1 to 3, substitutents independently selected from the group consisting of the substituents defined above under "Substituted"; especially being a heteroaryl radical selected from the group consisting of imidazolyl, thienyl, furyl, pyranyl, thiopyranyl, benzofuranyl, pyrrolinyl, pyrrolidinyl, imidazolidinyl, benzimidazolyl, pyrazolyl, pyrazinyl, pyrazolidinyl, thiazolyl, oxazolyl, pyridyl, pyrazinyl, pyrimidinyl, piperidyl, piperazinyl, pyridazinyl, morpholinyl, thiomorpholinyl, indolizinyl, isoindolyl, indolyl, benzimidazolyl, indazolyl, triazolyl, isoquinolyl, quinolyl, tetrahydroquinolyl, tetrahydroisoquinolyl, benzofuranyl, dibenzofuranyl, benzothiophenyl, dibenzothiophenyl, naphthyridinyl, quinoxalyl, quinazolinyl, carbazolyl, β-carbolinyl, phenanthridinyl, acridinyl, perimidinyl, phenanthrolinyl, furazanyl, phenazinyl, phenothiazinyl and phenoxazinyl, each of these radicals being unsubstituted or substituted by one to two radicals selected from the group consisting of lower alkyl, especially methyl or tert-butyl, and lower alkoxy, especially methoxy.

Cycloalkyl is preferably $C_3$-$C_{10}$-cycloalkyl, especially cyclopropyl, dimethylcyclopropyl, cyclobutyl, cyclopentyl, cyclohexyl or cycloheptyl, cycloalkyl being unsubstituted or substituted by one or more, especially 1 to 3, substitutents independently selected from the group consisting of the substituents defined above under "Substituted".

Aryl-lower alkyl is preferably lower alkyl that is substituted (preferably terminally or in 1-position) by unsubstituted or substituted aryl as defined above, especially phenyl-lower alkyl, such as benzyl.

Heterocyclyl-lower alkyl is preferably lower alkyl that is substituted (preferably terminally) by unsubstituted or substituted heterocyclyl as defined above.

Cycloalkyl-lower alkyl is preferably lower alkyl that is substituted (preferably terminally) by unsubstituted or substituted cycloalkyl as defined above.

Alkyl preferably has up to 20, more preferably up to 12 carbon atoms and is linear or branched one or more times; preferred is lower alkyl, especially $C_1$-$C_4$-alkyl.

Substituted alkyl is especially aryl-lower alkyl, heterocyclyl-lower alkyl or cycloalkyl-lower alkyl, wherein aryl-heterocyclyl or cycloalkyl are unsubstituted or substituted by one or more, preferably up to 4, subsituents independently selected from the substituents defined generally above.

An organic residue capable of binding to phosphorus preferably is any moiety that comprises 1 to 50 carbon atoms, that may saturated, unsaturated or partially saturated, wherein carbon atoms may be replaced with heteroatoms, especially selected from N, O, S, Se or P, with the proviso that the moiety is chemically stable. The organic residue may in addition be substituted, or unsubstituted, preferably as described above. In the case of $R_3$, "monovalent" means that the moiety is bound via one bond to the rest of the molecule (one hydrogen is replaced with this bond), in the case of $R_3$*, bivalent means that the moiety is bound via two bonds to the rest of the molecule, preferably in a manner so that 5 to 7-membered cyclic phosphorus metal complexes are formed.

Preferably, an organic residue capable of binding to phosphorus is selected from the group consisting of an unsubstituted or substituted moiety selected from the group consisting of aryl, heterocyclyl, cycloalkyl, aryl-lower alkyl, heterocyclyl-lower alkyl, cycloalkyl-lower alkyl, alkyl, aryloxy, heterocyclyloxy, cycloalkyloxy, aryl-lower alkyloxy, heterocyclyl-lower alkyloxy, cycloalkyl-lower alkyloxy and alkoxy, with the more general moieties mentioned preferably being defined as above.

A lithiating reagent is preferably an organolithium compound, preferably an alkyl-lithium, especially a lower alkyl-lithium, preferably n-butyllithium or hexyllithium, or in a broader aspect sec- or tert-butyllithium, or aryl-lithium, such as phenyllithium. The reaction preferably takes place in the presence of a tertiary nitrogen base, preferably a complex forming one, especially N,N,N',N'-tetramethylendiamine (TMEDA) in a liquid alkane or mixture of liquid alkanes, such as hexane(s), an (anhydrous, especially absolute) ether, especially a di-lower alkylether, such as diethylether, or a cyclic ether, such as tetrahydrofurane, at preferred temperatures between −70 and 50° C., especially between −50 and 45° C., more preferably between −30 and 40° C., preferably under inert gas, e.g. argon or nitrogen and under water-free conditions, e.g. using the Schlenk technology and equipment. For appropriate reaction conditions, see, e.g., Meyer, N., Seebach, D. Chem. Ber. 1980, 113, 1304.

An N,N-di-alkyl-formamide is preferably N,N-dimethyl-formamide (dimethylformamide). The reaction of a compound of the formula IIIA or IIIB with formamide preferably takes place in an appropriate solvent, e.g. as mentioned in the last paragraph, especially an alkane or alkanes mixture, such as hexane(s), at a preferred temperature from 0 to 50° C., e.g. from 10 to 40° C. The reaction with the N,N-dialkylformamide usually takes place in the reaction mixture resulting from the lithiation.

The temperature for the Grignard reaction is preferably elevated as then the selectivity towards the $C_2$-symmetric diol is increased, preferably at a temperature between −30° C. and the reflux temperature of the reaction mixture, more preferably between 20 and 70° C. The reaction preferably takes place in an aprotic solvent, especially an ether, such as a di-lower alkylether, or preferably a higher boiling ether, e.g. a cyclic ether, such as dioxane or especially tetrahydrofurane.

If a Grignard reagent $R_2MgX$ is used wherein $R_2$ is an organic moiety different from $R_1$ in formula IIIA or IIIB, this furnishes a mixture of 1,4-diols IVA or IVB. If in the Grignard reagent $R_2MgX$ $R_2$ is identical to $R_1$, a mixture of symmetrical diols is formed. In this case the $C_2$-symmetric diol is chiral AND enantiopure, whereas the $C_s$-symmetric diol is a meso compound. When the used Grignard reagent is of the type $R_2MgX$ wherein $R_1$ is different from $R_2$, again only two ENANTIOPURE diols are formed, one with local $C_2$-symmetry, and the other with local $C_s$-symmetry.

Surprisingly, in typical cases it is found, that at low temperature (−30° C.) an almost 1:1 ratio of the enantiomeric to the meso is observed, whereas at elevated temperature (65° C., refluxing THF) a mixture of the diols IVA or IVB ($C_2$-symmetry) and VA (with IVA) or VB (with IVB) ($C_s$-symmetry) in a ratio 4:1, or even higher, is obtained in 85% yield. The stereochemical assignment of IVA/IVB or VA/VB to be the chiral or meso-diol is based on the $^1$H-NMR of the acetonide. Here, IVA/IVB gives one signal and VA/VB two signals for the acetonide methyl groups, respectively, if $R_1=R_2$.

Halogen is preferably fluoro, chloro, bromo or iodo, more preferably chloro, bromo or iodo.

In the second preferred variant, the reaction with an aldehyde of the formula VI with a compound of the formula IIA or IIB preferably takes place directly in the lithiation mixture.

In this second variant, the resulting ration of IVA:VA or IVB:VB may typically be around 45:55, but the reaction allows for one pot synthesis and the use of starting materials that are conveniently accessible and thus provide a very pragmatic synthesis of the desired products which is highly advantageous.

The obtained products can be purified and, where required to isolate the pure isomers, separated according to standard methods, for example by chromatographic or solution crystallization methods.

In the first alternative for the manufacture of ligands of the formulae XA or XB*, the reaction of a compound of the formula IVA or IVB (or either a mixture of a compound of the formula IVA and of the formula VA given below, or a mixture of a compound of the formula IVB and of the formula VB given below; or a compound of the formula VA given below or of the formula VB given above), respectively, with a diaryl phosphonic acid halogenide of the formula VII, takes place in the presence of a base preferably takes place at preferred temperatures in the range from −10° C. to 80° C., preferably with a tertiary amine as base in an appropriate solvent, e.g. an ether, such as diethylether, a cyclic ether, such as tehtrahydrofurane, an aromatic hydrocarbon, such as toluene or xylene. The resulting product of the formula VIIIA or VIIIB, respectively, is then, in order to obtain a compound of the formula XA, XA*, XB or XB*, respectively, reacted with the corresponding compound of the formula IX (or the corresponding borane adduct of the formula $R_3$—$PH_2.BH_3$) or IX* (or the corresponding borane adduct of the formula $BH_3.H_2P$—$R_3$*-$PH_2.BH_3$) preferably with a tert-alkyl-lithium, such as tert-butyllithium, in an inert solvent, such as an aromatic solvent, e.g. toluene, anisol or xylene, or ethers, like tetrahydrofuran, or a di-lower alkanesulfoxide, such as dimethylsulfoxide, or dimethylformamide. Bases, such as lithium amides, alkoholates of alkalimetal hydroxydes, such as potassium tert-butylate or potassium hydroxide, N,N-di-(lower alkyl)-lower alkanoylamides, such as dimethylformamide, or dimethylsulfoxide, are also acceptable.

In the alternative route via the compounds of the formulae IVA* or IVB*, or VIIIA' or VIIIB', or IVA* and VA* or IVB* and VB*, the diol starting materials are reacted with the acyl halogenides preferably in the presence of a tertiary nitrogen base, such as triethylamine or pyridine to yield the corresponding hydroxy-acylated derivatives. Subsequently, the reaction with a compound of the formula IX or IX* takes place preferably in an inert solvent, such as a cyclic or acyclic ether, e.g. tetrahydrofurane or diethylether in the presence of a strong base, like lithium dialkylamide, such as lithium diethylamide, lithium diisopropylamide or a lower-alkyl-lithium, such as tert-butyllithium, or in a N,N-di-lower alkyl-lower alkanoylamide (especially N,N-dimethylformamide) and/or a di-lower alkanesulfoxide (especially dimethylsulfoxide) in the presence of a metal hydroxide, especially an alkali metal hydroxide, such as sodium or potassium hydroxide, or an alkali metal alcoholate, such as a sodium or potassium lower alkoxide.

In the alternative use of the compounds of the formula IVA or IVB for the production of ligands of the formula XIIA or XIIB, or XIIA* or XIIB*, the reaction with a compound of the formula XI or XI* preferably takes place under the following reaction conditions: The reaction with a compound of the formula XI or XI* preferably takes place in the presence of a base, especially a tertiary nitrogen base, such as pyridine or triethylamine. As solvent, inert solvents, especially ethers, such as tetrahydrofurane or diethylether, are preferred. The preferred reaction temperature lies in the range from −10 to 40° C. The reaction take place under exclusion of water and oxygen.

A leaving group L is preferably the moiety of an organic or inorganic acid remaining after removal of the acidic hydrogen, more preferably halogen, especially chloro or bromo.

The reaction of IVA or IVB or VA or VB with a compound of the formula XI or XI*, on the other hand, preferably takes place in an inert solvent such as an aromatic hydrocarbon, e.g. toluene or xylene, preferably at temperatures from 50° C. to reflux, e.g. at the reflux temperature of the reaction mixture.

In the third alternative use/method using the compounds of formula IVA or IVB in the manufacture of ligands, the reaction of a compound of the formula IVA or VIB with a compound of the formula XIII preferably takes place under the same conditions as described for the reaction of compounds of the formula IVA or IVB with a compound of the formula XI or XI*, the reaction with a compound of the formula XIII* preferably as described for the reaction of compounds of the formula IVA or IVB with a compound of the formula XI or XI*.

A leaving group L is preferably as defined above.

Complexes with transition metals of compounds of the formula XA, XB, XIIA, XIIB, XIVA and/or XIVB are preferably those of these ligands together with transition metals, especially of groups 3 to 12 of the periodic table of elements, including the lanthanides and actinides, especially of groups 4 to 12, most especially with rhodium, ruthenium, palladium, platin, iridium, nickel or cobalt, preferably with rhodium or ruthenium.

Free ligand positions may in addition be occupied by further ligands, and/or counterions may be present.

The formation of transition metal complexes of compounds of the formula XA, XB, XIIA, XIIB, XIVA and/or XIVB can follow methods that are known in the art. In particular, in the complex used as starting material the transition metal is utilized in coordination with ligands such as 1,5-cis-cyclooctadiene, norbornadiene, (ethylene)$_2$, triarylstilbene, benzonitrile and the like. Counterions may also be present, depending on the charge of the resulting complex, e.g. $BF_4^-$, $PF_6^-$, $SbF_5^-$ or $CF_3SO_3^-$, or lower alkanoates, such as acetate$^-$.

For the manufacture of the complex, for example the complex constituted from the selected transition metal and the original ligand to be replaced is dissolved in a suitable solvent, e.g. an ether, such as a cyclic ether, preferably tetrahydrofurane, a halogenated hydrocarbon, such as a chlorinated lower alkane, e.g. chloroform or dichloromethane, an alcohol, such as methanol or ethanol, an aromatic hydrocarbon, such a toluene or xylene, or an N,N-di-(lower alkyl)-lower alkanoylamide, such as dimethylformamide; if required, in the presence of a further anionic ligand able to coordinate to remaining free coordination positions, and the chiral ligand is added, either in the solid state or already dissolved in a suitable solvent. The progress of the reaction may, inter alia, be followed by detection of colour changes, precipitation of the product, NMR, GC, TLC or the like. At the end of the reaction, the solvent is removed and the chiral complex formed may be used as it is or it may be subjected to further standard purification steps known in the art in order to obtain a purified complex. Preferably, the complex formation takes place shortly or immediately before the use of the complex in organic synthesis, e.g. hydrogenation.

All reactions described herinbefore and hereinafter are preferably, where required, mandatorily, carried out under inert gas, e.g. argon or nitrogen and (where required or desirable) under water-free conditions, e.g. using the Schlenk technology and equipment and anhydrous (especially absolute) reagents and solvents.

The invention relates also to any novel single reaction step that forms part of the synthesis of compounds of the formula IVA and/or IVB, as well as of those of formula XA and/or XB, as well as of those of the formula XIIA and/or XIIB, as well as those of the formula XIVA and/or XIVB, or complexes of the ligands of the formulae XA, XB, XIIA, XIIB, XIVA and/or XIV, as well as to any novel intermediate formed during these synthesis steps.

Preferred embodiments of the invention can be found in the claims which are incorporated herewith by reference into the description.

Very preferred embodiments of the invention, especially of the C$_2$symmetric diols, and of ligands, as well as methods synthesis of the diols or ligands, respectively, according to the invention are mentioned in the following examples and claims. Also preferred are metal complexes comprising the ligand groups or ligands mentioned in the examples.

EXAMPLES

The following examples illustrate the invention without limiting the scope thereof.

Abbreviations:
n-BuLi n-butyllithium
NMR Nuclear Magnetic Resonance
THF tetrahydrofuran
TMEDA N,N,N',N'-tetramethylethylene diamine
Ph phenyl Example 1

Mixture of cis/trans (3R)-3-methyl-1,3-dihydro-isobenzofuran-1-ol: A solution of (1R)-1-phenylethanol (2.0 g, 16.37 mmol) and TMEDA (4.0 g, 34.35 mmol) in hexanes (20 mL) was cooled to −10° C., and then a solution of n-BuLi in hexanes (2.5 N, 13.8 mL, 34.38 mmol) was added within 15 minutes. The temperature was maintained in the range between −10 and −5° C. during the addition. The mixture was then allowed to warm to ambient temperature, and finally heated at 40° C. over night. To the formed beige suspension was then added DMF (2.4 g, 32.74 mmol) within 10 minutes, maintaining a temperature lower than 30° C. When the addition was complete, the mixture was stirred for another hour, and then hydrolyzed carefully with water. The organic layer was washed with water and brine, and dried (Na$_2$SO$_4$). Removal of the solvent left an orange oil (2.6 g), which was chromatographed on silica with ethyl acetate/hexane 1:2 to give the product as pale yellow oil (1.51 g, 61%) as a ca. 1:1 mixture of both diastereoisomers. $^1$H-NMR (CDCl$_3$, 300 MHz) δ 1.47 (d, J=6.2 Hz), 1.56 (d, J=6.5 Hz) (CH3); 3.97 (br s, OH); 5.22 (q, J=6.5 Hz), 5.48 (dq, J=6.2 Hz, J=0.9 Hz) (CH); 6.39 (br s), 6.46 (br s) (CH); 7.15-7.42 (m) (Ph-H). $^{13}$C-NMR (CDCl$_3$, 75 MHz) δ 21.86, 24.04 (CH3); 78.87, 79.60 (CH); 100.62, 101.04 (CH); 121.09, 121.20 (CH); 123.11, 123.19 (CH); 128.10, 128.12 (CH); 129.48, 129.49 (CH); 139.14, 139.21 (C); 144.01, 144.05 (C).

Example 2

Mixture of (R,R)-and (R,S)1-[2-(1-Hydroxy-ethyl)-phenyl]-ethanol: A solution of (3R)-3-methyl-1,3-dihydro-isobenzofuran-1-ol (500 mg, 3.32 mmol) in THF (5 mL) was heated to 60° C., and to this was added a solution of methyl magnesium bromide (2.77 mL 3 N solution in ether; 8.32 mmol) within 10 minutes. The mixture was heated at 60° C. for another 30 minutes. After cooling the mixture was poured in water. The product was extracted with ethyl acetate, and removal of the solvent gave an oil which was a 63:37 mixture of the chiral and meso-diol. When the same reaction was performed at a temperature of −30° C., the ratio of chiral:meso diol was 52:48. $^1$H-NMR (CDCl$_3$, 300 MHz) δ 1.50 (d, J=6.2 Hz, meso CH$_3$); 1.52 (d, J=6.4 Hz, chiral CH$_3$); 3.12 (br s, OH); 5.15 (q, meso CH); 5.19 (q, chiral CH); 7.25-7.32, 7.39-7.48 (2 m, Ph-H). $^{13}$C-NMR (CDCl$_3$, 75 MHz) δ 23.58 (meso CH$_3$); 24.80 (chiral CH$_3$); 65.50 (meso CH); 67.43 (chiral CH); 125.48 (meso Ph-CH); 126.19 (chiral Ph-CH); 128.00 (chiral Ph-CH); 128.09 (meso Ph-CH); 142.10 (meso Ph-C); 142.30 (chiral Ph-C).

From the diol mixture the meso-diol crystallizes readily. If racemic phenyl ethanol is used as a starting material, the obtained racemic chiral diol can be isolated from the mother liquors of the meso-diol crystallization via its highly crystalline di-benzoate (mp=126° C.), whereas the di-benzoate of the meso-diol is an oil at room temperature. Saponification of the racemic chiral di-benzoate and distillation (bp=127° C./0.01 mbar) gives the racemic chiral diol.

Example 3

Mixture of cis/trans (3R)-3-ethyl-1,3-dihydro-isobenzofuran-1-ol: A solution of (1R)-1-propylethanol (5.0 g, 36.7 mmol) and TMEDA (8.96 g, 77.1 mmol) in hexanes (50 mL) was cooled to −10° C., and then a solution of n-BuLi in hexane (10 N, 7.71 mL, 77.1 mmol+10 mL of hexane) was added within 15 minutes. The temperature was maintained in the range between −10 and −5° C. during the addition. The mixture was then allowed to warm to ambient temperature, and finally heated at 40° C. over night. To the formed beige suspension was then added DMF (5.37 g, 73.42 mmol) within 10 minutes, maintaining a temperature lower than 30° C. When the addition was complete, the mixture was stirred for another hour, and then hydrolyzed carefully with water. The organic layer was washed with water and brine, and dried (Na$_2$SO$_4$). Removal of the solvent left an orange oil (7.4 g), which was chromatographed on silica with ethyl acetate/hexane 1:2 to give the product as pale yellow oil (3.03 g, 50%) as a ca. 1:1 mixture of both diastereoisomers A/B. $^1$H-NMR (CDCl$_3$, 300 MHz) δ 0.93 (tr, J=7.3 Hz, A CH$_3$); 1.01 (tr, J=7.3 Hz, B CH$_3$); 1.62-2.03 (m, A+B CH$_2$); 3.87 (br s, B OH); 3.98 (br s, A OH); 5.11 (dd, J=4.4 Hz, J=6.5 Hz, B CH); 5.37 (ddd, J=2.1 Hz, J=4.2 Hz, J=6.6 Hz, A CH); 6.41 (s, B CH); 6.47 (d, J=2.1 Hz, A CH); 7.15-7.21, 7.27-7.43 (m, Ph H). $^{13}$C-NMR (CDCl$_3$, 75 MHz) δ 9.36 (A CH$_3$); 9.85 (B CH$_3$); 28.98 (A CH$_2$); 30.47 (B CH$_2$); 83.79 (A CH); 84.67 (B CH); 100.89 (B CH); 100.92 (A CH); 121.29 (A CH); 121.41 (B CH); 123.13 (A CH); 123.20 (B CH); 128.12 (A+B CH); 129.37 (B CH); 129.41 (A CH); 139.53 (B C); 139.72 (A C); 142.46 (A C); 142.54 (B C).

Example 4

Mixture of (R,R)- and (R,S)-1-[2-(1-Hydroxy-propyl)-phenyl]-propan-1-ol: A solution of (3R)-3-ethyl-1,3-dihydro-isobenzofuran-1-ol (500 mg, 3.04 mmol) in THF (5 mL) was heated to 60° C., and to this was added a solution of ethyl magnesium bromide (2.54 mL 3 N solution in ether; 7.61 mmol) within 5 minutes. The mixture was heated at 60° C. for another 30 minutes. After cooling the mixture was poured in water, and the pH was adjusted to 6 by adding 1 N HCl. The product was extracted with ethyl acetate, and removal of the solvent gave an oil (0.61 g, quant.) which was a 80:20 mixture of the chiral and meso-diol. $^1$H-NMR (CDCl$_3$, 300 MHz) δ 0.85 (tr, J=7.3 Hz, CH$_3$); 1.60-1.80 (m, CH$_2$); 2.81 (br s, OH); 4.72 ("tr", J=6.5 Hz, meso CH); 4.76 ("tr", J=6.2 Hz, chiral diol); 7.13-7.19 (m, Ph-CH); 7.24-7.34 (Ph CH). $^{13}$C-NMR (CDCl$_3$, 75 MHz) δ 9.66 (CH$_3$); 29.31 (meso CH$_2$); 30.20 (chiral CH$_2$); 69.40 (meso CH); 71.56 (chiral CH); 124.60 (meso Ph CH); 125.31 (chiral Ph CH); 126.36 (chiral Ph CH); 126.45 (meso Ph CH); 140.10 (Ph C).

Example 5

Mixture of cis/trans (3S)-3-isopropyl-1,3-dihydro-isobenzofuran-1-ol: A solution of (S)-2-methyl-1-phenylpropan-1-ol (50 g, 333 mmol) and TMEDA (81.2 g, 700 mmol) in hexanes (500 mL) was cooled to −10° C., and then a solution of n-BuLi in hexane (10 N, 70 mL, 700 mmol) was added within 15 minutes. The temperature was maintained in the range between −10 and −5° C. during the addition (exothermic). The mixture (now a yellow suspension) was then allowed to warm to ambient temperature, and finally heated for 17 hours at 40° C. The mixture was then allowed to cool to ambient temperature, and DMF (48.7 g, 666 mmol) was added slowly with 30 minutes, whilst the temperature was maintained below 30° C. The mixture was stirred for another hour, and then hydrolyzed carefully with water. The organic layer was washed with water and brine, and dried (Na$_2$SO$_4$) to leave 76.4 g of a dark brown oil. Distillation gave 25.9 g of the product (44%, bp=110-115° C./0.1 mbar), which was a mixture of diastereomers in a ratio of ca. 3(A):2(B) and solidified on prolonged standing. $^1$H/$^{13}$C-NMR (CDCl$_3$, 300 MHz, HSQC) δ/δ 0.76 (d, J=6.7 Hz, A CH$_3$)/16.09; 0.87 (d, J=6.7 Hz, B CH$_3$)/16.91; 1.05 (d, J=7.0 Hz A CH$_3$)/19.18; 1:10 (d, J=6.7 Hz, B CH$_3$)/19.32; 2.02-2.15 (m, A+B CHMe$_2$)/33.60 (A), 33.76 (B); 5.05 (d, J=3.8 Hz, B CH)/88.51; 5.31 ("tr", J=2.6 Hz, A CH)/87.70; 6.42 (s, B CH(OH)/100.71; 6.47 (d, J=2.4 Hz, A CH(OH)/101.21; 7.21 (d, J=6.7 Hz, Ar CH)/121.56 (A), 121.73 (B); 7.34 (m, Ar CH)/128.08 (A), 128.27 (B); 7.35 (m, Ar CH); 129.25 (B), 129.30 (A); 7.40 (m, Ar CH)/123.09 (A), 123.13 (B); 139.72 (B), 140.01 (A), 141.56 (A), 143.73 (B).

Example 6

(S)-1-[2-((S)-1-Hydroxy-2-methylpropyl)phenyl]-2-methyl-propan-1-ol: A solution of (3S)-3-isopropyl-1,3-dihydro-isobenzofuran-1-ol (2.0 g, 11.2 mmol) in THF (20 mL) was heated under an atmosphere of nitrogen at reflux. To this solution was added slowly a solution of isopropyl magnesium chloride (39.3 mmol) in THF (ca. 20 ml). This solution had been prepared from the commercial solution (19.6 ml 2N solution in ether), from which the solvent had been removed in vacuum, and where the residue was made up with THF to a volume of 20 ml). After the addition of the Grignard reagent was completed, the mixture was stirred for another 30 minutes, and then allowed to cool to ambient temperature. To the mixture was then added a 10% solution of ammonium chloride (ca. 30 ml). The aqueous layer was removed, and re-extracted with TBME (ca. 20 ml). From the combined organic layers the solvent was removed, and the residue was redissolved in TBME (ca. 50 ml). After washing with water and brine, the organic layer was dried (Na$_2$SO$_4$). Removal of the solvent left the product as an oil, 2.2 g (88%). There was only one isomer present by $^{13}$C-NMR, which turned out to be the (S,S)-diol. $^1$H/$^{13}$C-NMR (CDCl$_3$, HSQC/HMBC) δ/δ 0.783 (d, J=6.7 Hz)/20.02 (CH$_3$); 1.065 (d, J=6.5 Hz)/18.99 (CH$_3$); 2.02 (m)/35.29 (CHMe$_2$); 4.60 (d, J=7.6 Hz)/76.51 (CH(OH)); 2.38 br s (OH); 7.20-7.26 (m)/126.75 (Ar ortho-CH); 7.33-7.39 (m)/127.55 (Ar meta-CH); 141.41 (Ar ipso-C).

Example 7

(S)-1-(2-((S)-1-hydroxy-2-methylpropyl)phenyl)-3-methylbutan-1-ol: To a solution of (3S)-3-isopropyl-1,3-dihydro-isobenzofuran-1-ol (14.11 g, 0.129 mol) in THF (250 ml) was added at reflux temperature through a Teflon tube, which ended under the surface in the reaction mixture, a solution of isobutyl magnesium chloride (freshly prepared from 0.387 mol isobutyl chloride and 0.58 mol magnesium in 250 ml of THF) slowly within 20 minutes under efficient stirring. The mixture was then quenched with a solution of ammonium chloride (10%). The organic layer was separated, and the solvent was removed on the rotavapor. The residue was re-dissolved in ethyl acetate (200 ml), and this solution was washed with water (150 ml) and brine (150 ml). After drying and removal of the solvent the product was obtained as a yellow oil (31.5 g). $^1$H/$^{13}$C-NMR (300 MHz, CDCl$_3$, HSQC/HMBC) δ/δ 0.78 (d, J=6.9 Hz)/19.00, 1.04 (d, J=6.5 Hz)/20.22 (2 i-Pr CH$_3$); 0.95 (d, J=6.5 Hz)/23.87, 0.96 (d, J=6.5 Hz)/22.32 (2 i-Bu CH$_3$); 1.80 (m)/25.33 (i-Bu CHMe$_2$); 2.02 (m)/35.13 ((i-Pr CHMe$_2$); 1.47/1.72 (m)/48.03 (CH$_2$); 3.09 (br s, 2 OH); 4.53 (d, J=8.1 Hz)/77.55 (CH(OH)i-Pr); 5.08 (dd, J=4.7 Hz, J=9.5 Hz)/68.87 (CH(OH)i-Bu); 7.40 (m)/126.44 (Ar i-Bu ortho-CH); 7.21 (m)/127.37 (Ar meta-CH); 7.28 (m)/127.55 (Ar i-Pr ortho-CH); 7.23 (m)/127.71 (Ar meta-CH); 140.56 (Ar i-Pr ipso-C); 142.66 (Ar i-Bu ipso-CH).

Example 8

(3S)-3-(1-Hydroxy-ethyl)-thiophene-2-carbaldehyde: To a solution of (1S)-1-thiophen-3yl-ethanol (1.282 g, 10 mmol) in ether (11 ml) was added under a nitrogen atmosphere N,N,N',N'-tetramethyl ethylenediamine (2.44 g, 21 mmol) and this solution cooled to 0° C. Then was added a solution of n-BuLi (2.0 ml 10 N-solution in hexane, 20 mmol) within 10 minutes. The temperature was maintained in the range between 0-10° C. During this time a yellow suspension had formed, which was stirred for another 10 minutes at 0° C. The mixture was then allowed to warm to ambient temperature, and then DMF (1.462 g, 20 mmol) was added within 10 minutes. The temperature was kept below 30° over the addition period by cooling. When the addition was complete, the mixture was kept stirring for another 30 minutes and then water (25 ml) was added drop wise (!). The organic layer was isolated, and the aqueous layer was extracted twice with ethyl acetate (50 ml each). The combined organic layers were washed with brine (30 ml) and dried (Na$_2$SO$_4$). After removal of the solvent the residue was chromatographed on silica to give 1.284 g (82%) of the product as pale yellow oil. $^1$H-/$^{13}$C-NMR (CDCl$_3$, 300 MHz, HSQC) δ/δ 1.54 (d, J=6.7 Hz)/24.67 (CH$_3$); 3.70 (d, J=5.0 Hz) OH; 5.29 ("pent")/65.73 (CH(OH)); 7.21 (d, J=4.9 Hz)/128.83 (4-CH); 7.67 (d)/135.19 (5-CH); 137.43 (C-3); 155.34 (C-2); 9.97 (s)/183.33 (CHO).

Example 9

1-[3-(1-Hydroxy-ethyl)-thiophen-2-yl]-ethanol: A solution of (3S)-3-(1-Hydroxy-ethyl)thiophene-2-carbaldehyde (781 mg, 5.0 mmol) in THF (3.5 ml) was heated under a nitrogen atmosphere at reflux. To this solution was added at reflux temperature slowly a solution of methyl magnesium chloride (3.3 ml 3 N solution in THF, 10 mmol) within 10 minutes. The red solution was kept at reflux for another 30 minutes and after cooling to ambient temperature quenched carefully with water (3 ml). The resultant mixture was filtered through a pad of hyflo, and the filter cake was washed with little chloroform. From the filtrate the solvent was removed to leave 727 mg of a deep yellow oil (84%), which was a mixture of a major (A) and a minor (B) diastereomer. $^1$H-NMR (CDCl$_3$, 300 MHz) δ/δ 1.476 (d, J=6.5 Hz, B), 1.479 (d, J=6.4 Hz, A), 1.541 (d, J=6.4 Hz, A), 1.566 (d, J=6.4 Hz, B) (4 CH$_3$); 3.40 (br s, 1H), 3.70 (br s, 2H), 4.02 (br s, 1H) (4OH); 4.92 (q, couples with 1.479), 5.04 (q, couples with 1.476), 5.13 (q, couples with 1.541), 5.23 (q, couples with 1.566) (4 CH(OH)); 6.92 (d, J=5.3, couples with 7.08, B); 7.00 (d, J=5.3 Hz, couples with 7.114, A) (4 Thienyl CH).

Example 10

In analogy to the foregoing examples, the following compounds of formula IVA or IVB, wherein R$_1$ and R$_2$ are each n-propyl, are prepared:

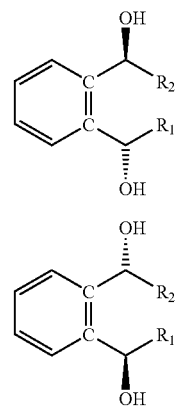

3A

3B

Example 11

Meso-1,5-Dimethyl-3-phenyl-1,5-dihydro-benzo[e][1,3,2]dioxaphosphepine 3-oxide: To a solution of meso 1-[2-(1-Hydroxyethyl)phenyl]-1-ethanol (17.4 g, 0.1 mol) in pyridine (24.8 g, 0.3 mol) was added at 0° C. a solution of phenyl phosphonic acid dichloride (20.4 g, 0.1 mol) in dichloromethane (10 ml). After stirring for another hour, the mixture was diluted with dichloromethane (ca. 100 ml), and 3N HCl was added until the pH was 3. The organic layer was separated, and the aqueous layer was extracted once more with dichloromethane. After removal of the solvent and trituration of the residue with pentane the product was obtained as colourless crystals, 30.1 g, quant. $^1$H-NMR (CDCl$_3$) δ 1.87 (d, J=6.4 Hz, CH$_3$); 6.25 (dq, CHCH$_3$); 7.28-7.78 (m, Ar CH). $^{31}$P-NMR δ 20.35.

Example 12

(1R,5S)-1,5-Diethyl-3-phenyl-1,5-dihydro-benzo[e][1,3,2]dioxa-phosphepine-3-oxide: To a solution of (R,S)-1-[2-

(1-Hydroxy-propyl)-phenyl]-propan-1-ol (1.0 g, 5.15 mmol) in pyridine (1.22 g, 15.4 mmol) was added under exclusion of moisture phenyl phosphonic acid dichloride (1.0 g, 5.15 mmol). There is an exotherm and instant formation of pyridinium hydrochloride. The mixture was stirred over night. By $^{31}$P-NMR of the crude mixture there was complete conversion, and only one of two possible diastereoisomers present. After addition of HCl (5 ml of 4 N solution) the product was extracted with TBME (20 ml).

Chromatography of the crude product on silica (CHCl$_3$/ethyl acetate 1:2 v:v) gave 1.1 g (67.5%) of colourless crystals, mp=133-137° C. $^1$H/$^{13}$C-NMR (CDCl$_3$, HSQC/HMBC) δ/δ 1.19 (tr, J=7.2 Hz)/11.24 (CH$_3$); 2.15-2.26 (m)/26.97 (d, J=7.2 Hz) (CH$_2$); 5.89 (m)/75.40 (d, J=6.8 Hz) (CH); 7.47 (m)/126.39 (s) (Ar ortho-CH); 127.62 (d, J=197 Hz) (Ph ipso-C); 7.38 (m)/128.30 (d, J=15.5 Hz) (Ph meta-CH); 7.39 (m)/128.66 (s) (Ar meta-CH); 7.49 (m)/132.75 (d, J=3.4 Hz) (Ph para-CH); 7.73 (m)/131.93 (d, J=10.2 Hz) (Ph ortho-CH); 139.36 (Ar ipso-C). $^{31}$P-NMR (CDCl3) δ 20.95.

Example 13

(1S,5S)-1,5-Diethyl-3-phenyl-1,5-dihydro-benzo[e][1,3,2]dioxa-phosphepine-3-oxide: A solution of (R,S)-1-[2-(1-Hydroxy-propyl)-phenyl]-propan-1-ol (4.0 g, 20.6 mmol) in pyridine (4.89 g, 61.7 mmol) was cooled with an ice-bath. Then phenyl phosphonic acid dichloride (4.03 g, 20.6 mmol) was added drop wise. The mixture was allowed to warm to ambient temperature, and stirred over night. To the mixture was then added HCl (ca. 20 ml 4N solution) and TBME (ca. 50 ml). The organic layer was separated, dried (sodium sulfate), and after removal of the solvent the product remained as a colourless oil. Yield: 5.88 g (90.3%). $^1$H/$^{13}$C-NMR (CDCl$_3$, HSQC/HMBC) δ/δ 1.05 (tr, J=7.4 Hz)/11.05 (CH$_3$); 1.13 (tr, J=7.6 Hz)/10.48 (CH$_3$); 2.05-2.21 (m)/27.82 (d, J=8.9 Hz), 30.61 (d, J=9.4 Hz) (2 CH$_2$Me); 5.42 (ddd, J=4.7 Hz, J=5.8 Hz, J=8.5 Hz)/80.30 (d, J=7.6 Hz) (CHEt); 5.75 (ddd, J=3.8 Hz, J=5.3 Hz, J=7.4 Hz)/80.47 (d, J=7.3 Hz) (CHEt); 7.24/126.73 (Ar CH); 7.24/127.18 (Ar CH); 7.24/128.12 (Ar CH); 7.31/128.59 (Ar CH); 7.40/128.47 (d, J=15.2 Hz) (Ph meta-CH); 128.93 (d, J=192 Hz) (Ph ipso-C); 7.51/132.47 (d, J=3.1 Hz) (Ph para-CH); 7.73/131.74 (d, J=9.8 Hz) (Ph ortho-CH); 137.66, 138.92 (2 Ar ipso-C). $^{31}$P-NMR (CDCl$_3$) δ 19.26.

Example 14

(1S,5S)-1,5-Diisopropyl-3-phenyl-1,5-dihydro-benzo[e][1,3,2]dioxa-phosphepine 3-oxide: A solution of (S)-1-[2-((S)-1-Hydroxy-2-methylpropyl)phenyl]-2-methyl-propan-1-ol (1.0 g, 4.9 mmol) in pyridine (1.16 g 14.7 mmol) was cooled with an ice-bath. To this mixture was then added drop wise phenyl phosphonic acid dichloride (0.96 g, 4.9 mmol). After stirring for 90 minutes the reaction was complete by $^{31}$P-NMR. To the mixture was then added TBME (ca. 20 ml) and hydrochloric acid (ca. 5 ml 4N-solution). The organic layer was separated, dried (Na$_2$SO$_4$), and removal of the solvent left the product as an oil. Yield 1.50 g (89%). $^1$H/$^{13}$C-NMR (CDCl$_3$, HSQC/HMBC) δ/δ 0.965 (d, J=6.5 Hz)/20.38 (CH$_3$); 1.075 (d, J=6.5 Hz)/19.05 (CH$_3$); 1.106 (d, J=6.5 Hz)/17.71 (CH$_3$); 1.112 (d, J=6.7 Hz)/20.38 (CH$_3$); 2.37 (m)/34.58 (d, J=8.3 Hz) (CHMe$_2$); 2.49 (m)/31.28 (d, J=7.6 Hz) (CHMe$_2$); 5.17 (dd, J=5.6 Hz, J=7.6 Hz)/83.85 (d, J=8.9 Hz) (CH(i-Pr)); 5.53 (dd, J=3.8 Hz, J=5.9 Hz)/84.36 (d, J=7.6 Hz) (CH(i-Pr)); 7.24 (m)/127.28 (Ar CH); 7.24 (m)/127.93 (Ar CH); 7.24 (m)/127.95 (Ar CH); 7.27 (m)/128.31 (Ar CH); 7.37 (m)/128.43 (Ar CH); 7.37 (m)/128.43 (d, J=15.1 Hz) (Ph meta-CH); 129.12 (d, J=193 Hz) (Ph ipso-C); 7.47 (m)/132.38 (d, J=3.0 Hz) (Ph para-CH); 7.70 (m)/131.63 (d, J=9.8 Hz) (Ph ortho-CH); 137.23 (s), 138.48 (d, J=1.0 Hz) (2 Ar ipso-C). $^{31}$P-NMR (CDCl$_3$) δ 18.72.

Example 15

Reaction of A with phenylphosphonic acid chloride gives the cyclic phosphonate ester B in quantitative yield. When B is reacted with a primary phosphine in the presence of a suitable base, such as tert-butyllithium or lithium diethyl amide, under reflux in toluene, the hitherto unknown benzophospholanes C are formed. There are no limitations to R$_3$, as long as this can bind stable to phosphorus. It is worthy to note, that there is little precedence for nucleophilic substitution with inversion of benzylic positions. A cyclic sulfate of A (with R=Me), which should react similarly like B, decomposes very rapidly after it has been prepared.

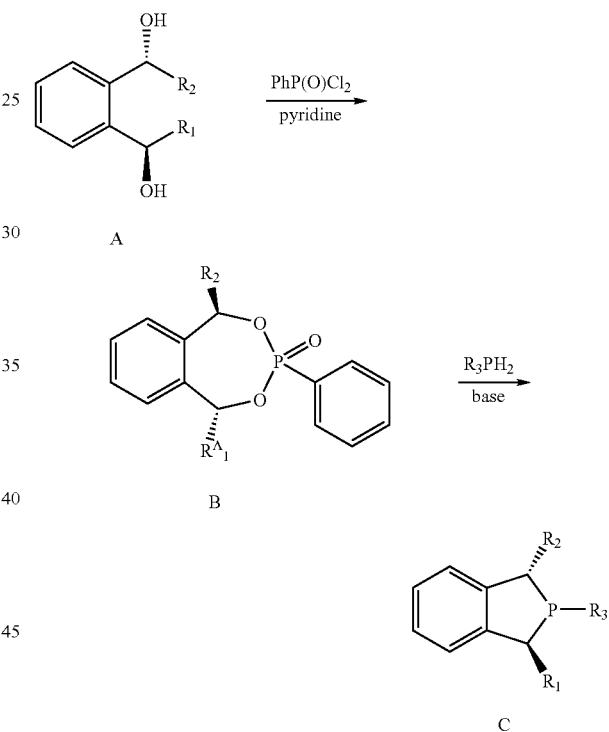

R$_1$ and R$_2$ have the meanings indicated above for compounds of the formula IVA or IVB, R$_3$ is an organic moiety that can be bound to phosphorus.

An alternative variant for the preparation of C is as follows:

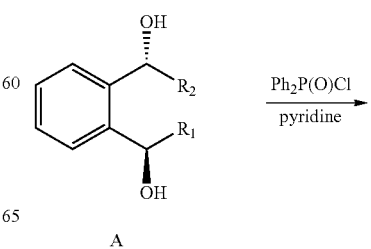

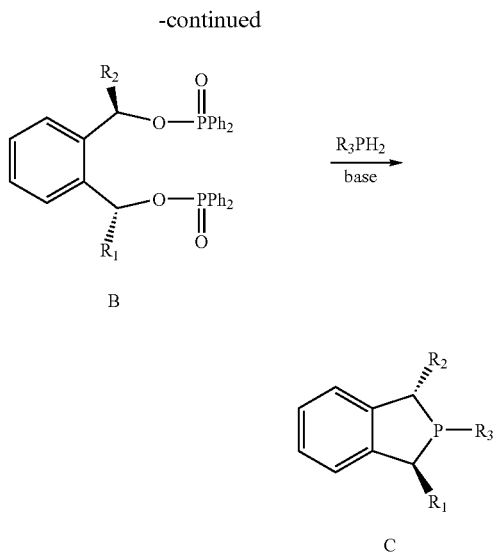

B

R₁, R₂ and R₃ are as defined above.

Example 16

Preparation and ee-determination of diphenyl-phosphinic acid 1-phenyl-ethyl ester: To a solution of (R)-1-phenylethanol (12.21 g, 0.1 mol, 70% ee) in pyridine (15.8 g, 0.2 mol) and dichloromethane (50 mL) was added drop wise within 10 minutes a solution of diphenylphosphonic acid chloride (23.6 g, 0.1 mol) in dichloromethane (100 ml). After three hours started the precipitation of pyridine hydrochloride, and the conversion was ca. 85% by $^{31}$P-NMR. The mixture was stirred at ambient temperature for another hour, and then the dichloromethane was removed on the rotavapor (50° C., 500 mbar). To the residue was added hydrochloric acid (50 ml 4N solution), and the product was extracted with ether. The organic layer was washed with water (twice ca. 100 ml), dried (Na₂SO₄), and removal of the solvent gave 29.2 g of an oil which was crystallised from di-isopropyl ether to give 17.41 g crystals, mp. 81-81.5° C. The ee-determination of this material gave an ee of 92%. The melting point of the racemic compound is 73° C. Ee assay for the phosphonate: ChiralPack AD, n-hexane/ethanol 97:3, 18.92 min (R-ester) and 21.81 min (S-ester). $^1$H/$^{13}$C-NMR (CDCl₃, 300 MHz) δ/δ 1.66 (d, J=6.4 Hz)/25.40 (d, J=3.1 Hz) (CH₃); 5.52 (dq, J=9.1 Hz)/74.84 (d, J=5.7 Hz) (CHMe); 7.27 (m)/126.10 (Ar ortho-CH); 7.26 (m)/128.09 (Ar para-CH); 7.26 (m)/128.46 (d, J=13.0 Hz) (Ph meta-CH); 7.26 (m)/128.61 (Ar meta-CH); 7.41 (m)/128.62 (d, J=13.2 Hz) (Ph meta-CH); 7.82 (m)/131.68 (d, J=10.0 Hz) (Ph ortho-CH); 131.79 (d, J=134.5 Hz) (Ph ipso-C); 7.63 (m)/132.03 (d, J=10.3 Hz) (Ph ortho-CH); 7.42 (m)/132.10, 132.20 (2 d, J=2.9 Hz), (2 Ph para-CH); 132.71 (d, J=139.3 Hz) (Ph ipso-C); 142.28 (d, J=4.8 Hz) (Ar ipso-C). $^{31}$P-NMR δ 31.72.

Example 17

Preparation of diphenyl-(1-phenyl-ethyl)-phosphane and determination of the optical yield for this alkylation reaction: In a Schlenk flask under an atmosphere of nitrogen was added to a solution of diethylamine (0.185 g, 2.53 mmol) in THF (2 ml) a solution of n-BuLi (0.7 ml 1.6 N solution, 1.12 mmol), and after stirring for two minutes diphenyl-phosphine (0.186 g, 1 mmol) which led to a change of the color to yellow. Without delay was then a solution of diphenyl-phosphinic acid 1-phenyl-ethyl ester (0.322 g, 1 mmol) in THF (2 ml) added drop wise within ca. three minutes. The color was fading, and after ca. half of the phosphonate had been added, a precipitate formed. After stirring for another 10 minutes, sodium hydroxide (1.0 ml 40% solution), water (3 ml), and TBME (10 ml) was added. After stirring for five minutes two colourless layers had formed. Removal of the aqueous layer and evaporation of the TBME leaves diphenyl-(1-phenyl-ethyl)-phosphane as a solid. When racemic diphenyl-phosphinic acid 1-phenyl-ethyl ester was utilized in this preparation, the product was recrystallised from methanol (5 ml), filtered off and dried to give 210 mg (71% yield). This material was converted into the phosphine oxide via oxidation with hydrogen peroxide and used to establish an ee-assay: Chiracel OD, n-hexane/ethanol 97:3, 14.76 min (S-oxide) and 16.803 min (R-oxide).

When diphenyl-phosphinic acid 1-phenyl-ethyl ester of an ee of 92% was used in the above reaction, the ee of the phosphine oxide was 87.85%, which means that the optical yield for the inversion is 95%.

Analytical data for diphenyl-(1-phenyl-ethyl)-phosphane: $^1$H/$^{13}$C-NMR (CDCl₃, 300 MHz HSQC/HMBC) δ/δ 1.28 (dd, J=7.0 Hz, J=14.0 Hz)/20.22 (d, J=20.4 Hz) (CH₃); 3.41 (dq, J=7.0 Hz)/39.58 (d, J=12.5 Hz) (CHMe); 7.18 (m)/126.35 (1 C, d, J=2.3 Hz) (Ar para-CH); 7.17 (m)/128.05 (2 C, d, J=6.5 Hz) (Ar ortho-CH); 7.24 (m)/128.46 (d, J=0.6 Hz) (Ph para-CH); 7.24 (m)/128.48 (d, J=1.0 Hz) (Ar meta-CH); 7.22 (m)/128.68 (d, J=7.6 Hz) (Ph meta-CH); 7.46 (m)/128.75 (d, J=7.4 Hz)) (Ph meta-CH); 7.46 (m)/129.42 (d, J=0.9 Hz) (Ph para-CH); 7.15 (m)/133.32 (d, J=17.9 Hz) (Ph ortho-CH); 7.69 (m)/134.33 (d, J=20.8 Hz) (Ph ortho-CH); 137.12 (d, J=16.1 Hz) (Ph ipso-C); 137.70 (d, J=15.0 Hz) (Ph ipso-C); 143.64 (d, J=8.8 Hz) (Ar ipso-C). $^{31}$P-NMR δ 3.73. Analytical data for diphenyl(1-phenyl-ethyl)-phosphane oxide: $^{31}$P-NMR δ 37.89.

Example 18

Diphenyl-phosphinic acid 1-{2-[1-(diphenyl-phosphinoyloxy)-ethyl]-phenyl}-ethyl ester: To a solution of racemic chiral 1-[2-(1-Hydroxy-ethyl)-phenyl]-ethanol (1.0 g, 6.016 mmol) in pyridine (3.8 g, 48.1 mmol) was added drop wise diphenyl phosphonic acid chloride (2.85 g, 12.05 mmol) within 5 minutes. After three minutes the mixture had warmed to 40° C., and the reaction was moderated by cooling and the addition of methylene chloride (10 ml). The mixture was stirred at ambient temperature for 3½ hours, and the conversion monitored by $^{31}$P-NMR. There was still a small amount of mono-phosphonate present, and thus another 0.5 ml of the phosphonic acid chloride was added, and the stirred for another two hours. Then water (0.5 ml) was added, and the mixture stirred for another hour. To the mixture was then added under efficient stirring ether (50 ml), and 4N HCl (20 ml). Stirring was stopped, the organic layer was separated and extracted with 2N NaOH (130 ml). The organic layer was then separated, dried (Na₂SO₄), and removal of the solvent left 3.5 g of an oil. This was diluted with di-isopropyl ether (ca. 15 ml, two phases), and after stirring for an hour the product started to crystallize. Yield 1.38 g (40.5%), mp=147-148° C. $^1$H/$^{13}$C-NMR (CDCl₃, 300 MHz, HSQC) δ/δ 1.27 (d, J=6.3 Hz)/25.42 (d, J=2.9 Hz) (CH₃); 5.48 (dq, J=9.6 Hz)/70.59 (d, J=5.3 Hz) (CHMe); 7.54 (m)/125.43 (Ar meta-CH);

7.28 (m)/128.20 (s) (Ar ortho-CH); 7.24 (m)/128.45 (d, J=13.0 Hz), 7.41 (m)/128.60 (d, J=13.0 Hz); (Ph meta-CH); 131.53 (d, J=134 Hz) (Ph ipso-C); 7.79 (m)/131.54 (d, J=10.2 Hz), 7.55 (m)/131.94 (d, J=10.2 Hz) (Ph ortho-CH); 7.33 (m)/132.11 (d, J=2.9 Hz), 7.44 (m)/132.19 (d, J=2.9 Hz) (Ph para-CH); 132.38 (d, J=139 Hz) (Ph ipso-C); 138.37 (d, J=4.8 Hz) (Ar ipso-C). $^{31}$P-NMR δ 31.74.

Example 19

1,3-Dimethyl-2-phenyl-2,3-dihydro-1H-isophosphindole: Under an atmosphere of nitrogen a Schlenk flask was charged with diethylamine (0.584 g, 8 mmol), to which a solution of n-BuLi (2.5 ml 1.6 N-solution in hexanes, 4 mmol) was added drop wise under efficient stirring. To the slightly hazy solution was then added phenyl phosphine (0.110 g, 1 mmol) which led to the formation of a yellow solution. This mixture was diluted with THF (2 ml), and immediately afterwards was added under efficient stirring a solution of diphenyl-phosphinic acid 1-{2-[1-(diphenyl-phosphinoyloxy)-ethyl]-phenyl}-ethyl ester (0.567 g, 1 mmol) in THF (made up to 2 ml total volume) drop wise over two minutes into the Schlenk flask. When the addition was complete, the mixture was stirred for another ten minutes. To the mixture was then added water (3 ml), sodium hydroxide (1 ml 40% solution in water), and TBME (15 ml). The mixture was stirred for 10 minutes, by which time two clear layers had formed. The aqueous layer was removed via syringe, and the organic layer was dried (Na$_2$SO$_4$). Removal of the solvent in vacuum left the product as colourless oil. $^1$H/$^{13}$C-NMR (CDCl$_3$, 300 MHz, HSQC/HMBC, indices A/B relate to syn/anti to P-lone pair) δ/δ 1.21 (dd, J=7.3 Hz, J=11.2 Hz)/14.45 (s) (B-CH$_3$); 1.62 (dd, J=7.7 Hz, J=18.6 Hz)/21.73 (d, J=29.9 Hz) (A-CH$_3$); 3.59 (dq, J=16.6 Hz)/40.04 (d, J=8.5 Hz) (A CHMe); 3.77 (dq, J=2.3 Hz)/35.57 (d, J=13.5 Hz) (B CHMe); 7.17 (m)/125.27 (d, J=1.1 Hz) (A Ar ortho-CH); 7.26 (m)/126.88, 7.26/127.22 (2 Ar meta-CH); 7.36 (m)/125.60 (d, J=1.3 Hz) (B Ar ortho-CH); 7.21 (m)/128.15 (d, J=7.2 Hz) (Ph meta-CH); 7.27 (m)/129.26 (d, J=1.0 Hz) (Ph para-Ch); 7.27 (m)/133.81 (d, J=19.8 Hz) (Ph ortho-CH); 135.90 (d, J=22.1 Hz) (Ph ipso-C); 145.09 (d, J=3.8 Hz) (B Ar ipso-C); 149.04 (d, J=2.3 Hz) (A Ar ipso-C). $^{31}$P-NMR δ 22.14.

Example 20

The following ligands can be prepared in analogy to the methods described in example 15:

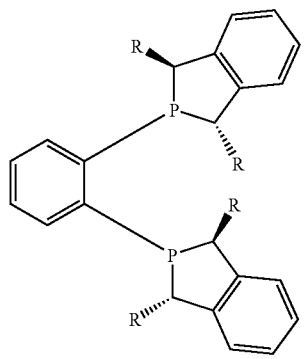
X

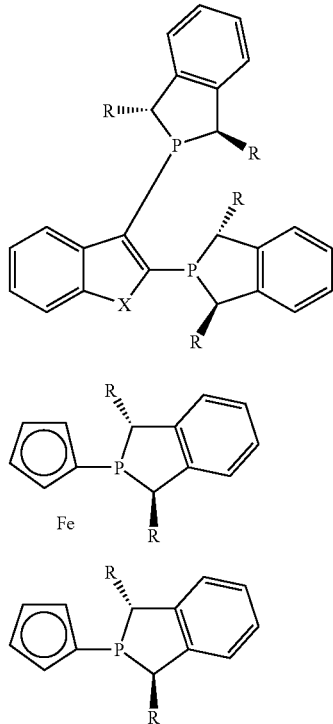
Y

Z

R=identical and selected from methyl, ethyl, isopropyl, n-propyl and tert-butyl; X=O, S or N.

Example 21

Another use of diols such as A is their conversion into ligands of type D or E. The synthesis of these compounds follows standard procedures where a phosphorus compound with a suitable leaving group X is reacted with the diol.

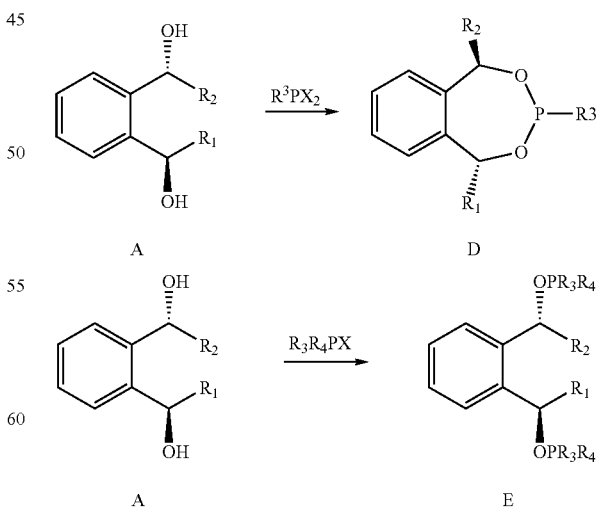

Herein, R$_3$ or R$_4$ may be any group that can be bound to phosphorus.

Example 22

The following ligands can be prepared in analogy to the methods described in example 21:

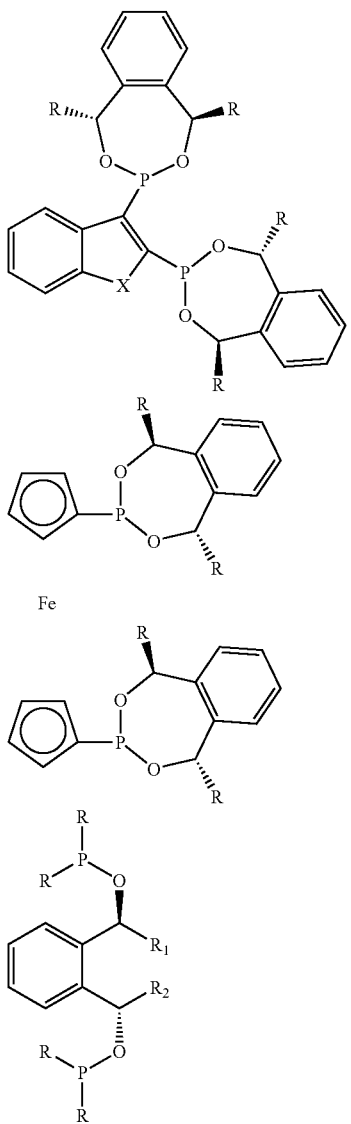

X=N, O or S. R=methyl, ethyl, isopropyl, tert-butyl; $R_1=R_2$=selected from alkyl, especially lower alkyl, aryl, especially phenyl, or heterocyclyl, especially 2-thienyl.

Example 23

(1RS,5RS)-1,5-Dimethyl-3-phenyl-1,5-dihydro-benzo[e][1,3,2]dioxaphosphepine: A solution of 1-[2-(1-Hydroxyethyl)-phenyl]-ethanol (1.0 g, 6.02 mmol) and bis-(dimethylamino)phenylphosphine (1.18 g, 6.02 mmol) in toluene (5 ml) was heated at reflux under a nitrogen atmosphere until all of the bis-(dimethylamino)phenylphosphine had been consumed ($^{31}$P-NMR, 24 h). The solvent was then removed in vacuum to leave the product as a colourless oil in almost quantitative yield. $^1$H/$^{13}$C-NMR (CDCl$_3$, 300 MHz, HSQC/HMBC/NOE): δ/δ 1.59 (d, 3H, J=6.7 Hz)/21.77 (d, J=2.2 Hz) Ph anti-CH$_3$; 1.90 (d, 3H, J=6.4 Hz)/23.51 (d, J=7.0 Hz) Ph syn-CH$_3$; 5.41 (p, 1H, $J_{P,H}$≈7 Hz)/70.72 (d, J=6.1 Hz) Ph syn-CHCH$_3$); 5.63 (p, J=$J_{P,H}$≈6.4 Hz)/74.72 (d, J=9.6 Hz) Ph anti-CHCH$_3$); 7.19/126.65 ortho-CH); 7.30/126.65 ortho-CH); 7.21/127.35 meta-CH); 7.28/127.58 meta-CH); 7.41/128.33 (d, J=4.6 Hz) Ph meta-CH); 7.68/129.80 (d, J=20.1 Hz) Ph ortho-CH); 7.41/130.28 (d, J=0.6 Hz) Ph p-CH); 141.03 (d, J=0.9 Hz) ipso-C); 141.65 (d, J=32.6 Hz) Ph ipso-C); 142.54 (d, J=0.6 Hz) ipso-C). $^{31}$P-NMR: δ 154.2.

What is claimed is:

1. A process for the preparation of $C_2$-symmetric 1,4-diols of the formula IVA or IVB having a high enantiomeric purity

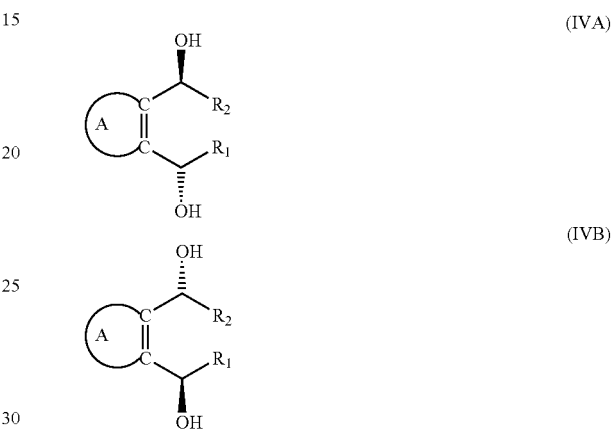

wherein ring A which includes the shown double bond forms a mono-, di- or polycyclic aromatic or heteroaromatic ring and $R_1$ and $R_2$ are, independently of each other, an organic moiety, the process comprising reacting an α-(aryl or heteroaryl)-α-substituted alkanol compound of the formula IA (for the synthesis of a compound of the formula IVA) or IB (for the synthesis of a compound of the formula IVB)

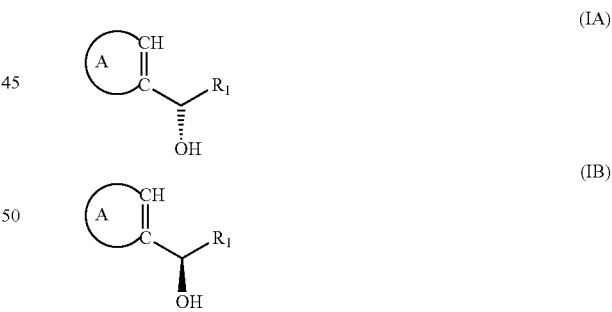

wherein ring A and $R_1$ are as defined under formula IVA and IVB, with a lithiating reagent, obtaining an intermediate of the formula IIA (from IA) or IIB (from IB),

-continued

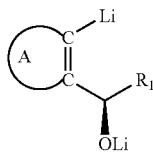
(IIB)

wherein ring A and R$_1$ have the meanings given under compounds of the formulae IVA and IVB, said process further comprising reacting the lithiated product of the formula IIA or IIB, respectively, with an N,N-di-alkyl-formamide to form a hemiacetal compound of the formula IIIA (from IIA) or IIIB (from IIB),

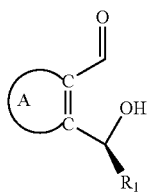
(IIIA′)

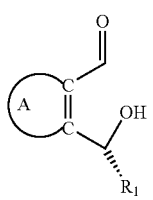
(IIIB′)

wherein ring A, R$_1$ and R$_2$ have the meanings indicated for compounds of the formula IVA and IVB, and subsequently with a Grignard reagent of the formula R$_2$MgX wherein R$_2$ is an organic moiety and X is halogen or, alternatively, using corresponding lithium, zinc or other metal comprising compounds that allow for introduction of R$_2$; to yield the corresponding compounds of formula IVA (from IIIA) and IVB (from IIIB).

2. A process for the preparation of a ligand of the formula XA, XA*, XB or XB* given below, said process comprising reacting a compound of the formula IVA (for the synthesis of a compound of the formula XA) or IVB (for the synthesis of a compound of the formula XB) obtained according to claim 1 with an aryl phosphinic acid halogenide of the formula VII;

$$Ar\text{---}P(=O)(Hal)_2 \quad \quad (VII)$$

wherein Ar is aryl and Hal is halogen, in the presence of a base resulting in the formation of a phosphonate ester compound of the formula VIIIA (from IVA) or VIIIB (from IVB), respectively,

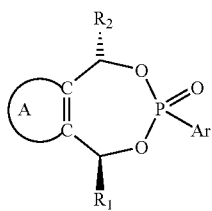
(VIIIA)

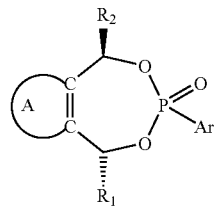
(VIIIB)

wherein ring A, R$_1$ and R$_2$ have the meanings indicated for compounds of the formula IVA and IVB and Ar is aryl, and then reacting a compound of the formula VIIIA or VIIIB with a phosphine of the formula IX or IX*, $$R_3\text{---}PH_2 \quad \quad (IX)$$

$$H_2P\text{---}R_3*\text{---}PH_2 \quad \quad (IX*)$$

(or the corresponding borane adduct thereof) wherein R$_3$ is a monovalent and R$_3$* is a bivalent organic moiety that can be bound to phosphorus, resulting in a phospholane compound of the formula XA or XA* (from VIIIA); or XB or XB* (from VIIIB), respectively,

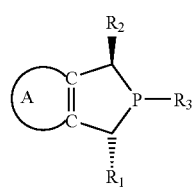
(XA)

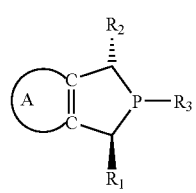
(XB)

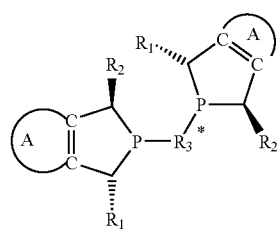
(XA*)

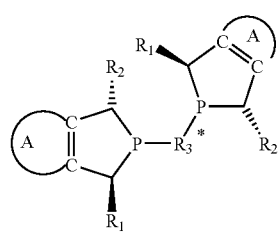
(XB*)

wherein ring A, R$_1$ and R$_2$ have the meanings indicated for compounds of the formula IVA or IVB and R$_3$ or R$_3$* is as defined under formulae IX and IX*, respectively.

3. A ligand of the formula XA, XA*, XB or XB*, as shown and defined in claim 2.

4. A transition metal complex comprising a ligand of the formula XA, XA*, XB or XB*, as shown and defined in claim 2.

5. A process for the preparation of a ligand of the formula XA, XA*, XB or XB* given below, said process comprising reacting a compound of the formula IVA (for the synthesis of a compound of the formula XA) or IVB (for the synthesis of a compound of the formula XB) obtained according to claim 1 with an aryl phosphinic acid halogenide of the formula VII';

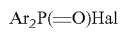  (VII')

wherein Ar is aryl and Hal is halogen, in the presence of a base resulting in the formation of a compound of the formula VIIIA' (from IVA) or VIIIB' (from IVB), respectively,

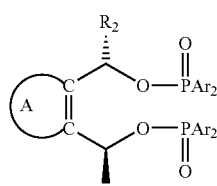  (VIIIA')

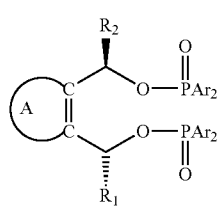  (VIIIB')

wherein ring A, $R_1$ and $R_2$ have the meanings indicated for compounds of the formula IVA and IVB in claim 1 and Ar is aryl, and then reacting a compound of the formula VIIIA' or VIIIB' with a phosphine of the formula IX or IX*,

  (IX)

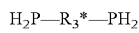  (IX*)

(or the corresponding borane adduct thereof) wherein $R_3$ is a monovalent and $R_3^*$ is a bivalent organic moiety that can be bound to phosphorus, resulting in a phospholane compound of the formula XA or XA* (from VIIIA); or XB or XB* (from VIIIB), respectively,

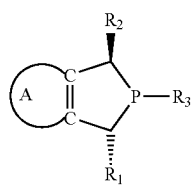  (XA)

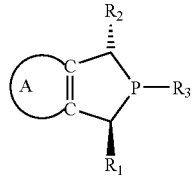  (XB)

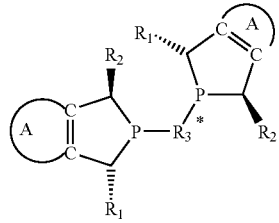  (XA*)

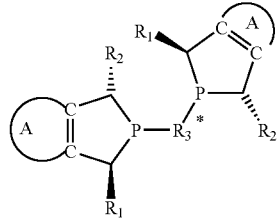  (XB*)

wherein ring A, $R_1$ and $R_2$ have the meanings indicated for compounds of the formula IVA or IVB in claim 1 and $R_3$ or $R_3^*$ is as defined under formulae IX and IX*, respectively.

6. A process for the preparation of a compound of the formula XA, XA*, XB or XB*,

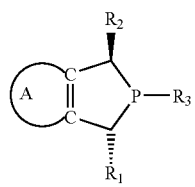  (XA)

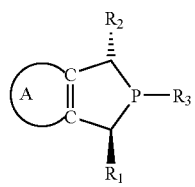  (XB)

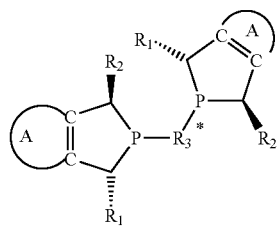  (XA*)

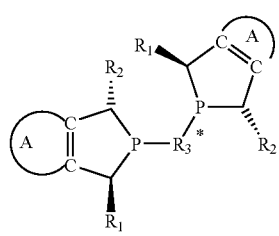  (XB*)

wherein ring A, $R_1$ and $R_2$ have the meanings indicated for compounds of the formula IVA or IVB in claim 1 and $R_3$ or $R_3^*$ is as defined under formulae IX and IX*, respectively said process comprising reacting a compound of the formula IVA or IVB given in claim 1, or a mixture of a compound of the formula IVA and VA, or of a compound of the formula IVB and VB,

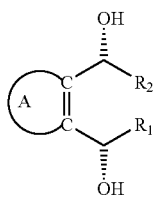

(VA)

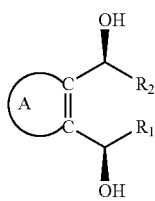

(VB)

wherein ring A, $R_1$ and $R_2$ have the meanings indicated for compounds of the formula IVA and IVB, with an agent introducing an acyl protecting group, obtaining the corresponding bis-hydroxy-protected compounds of the formula IVA* (from IVA), IVB* (from IVB), or mixtures of a compound of the formula IVA* and VA* (from a mixture of a compound of the formula IVA and VA) or of a compound of the formula IVB* and VB* (from a mixture of a compound of the formula IVB and VB),

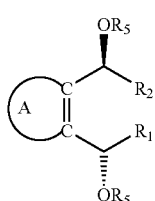

(IVA*)

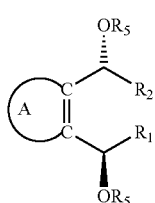

(IVB*)

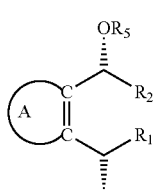

(VA*)

-continued

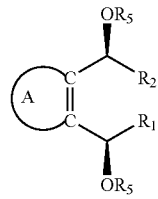

(VB*)

wherein ring A, $R_1$ and $R_2$ have the meanings indicated for compounds of the formula IVA and IVB and $R_5$ is acyl, an then reacting the compound or compounds to the corresponding compounds of the formulae XA shown above with a compound of the formula IX, $$R_3-PH_2 \quad (IX)$$

or a borane adduct thereof, wherein $R_3$ is a monovalent organic moiety that can be bound to phosphorus, or for a compound of the formula XA* shown above with a compound of the formula IX*, $$H_2P-R_3^*-PH_2 \quad (IX^*)$$

or a borane adduct thereof, wherein $R_3^*$ is a bivalent organic moiety that can be bound to phosphorus, in both cases starting from a compound of the formula IVA* (alone or optionally in mixture with a compound of the formula VA*);

or of the formula XB shown above with a compound of the formula IX shown above or a borane adduct thereof, or to a compound of the formula XB* shown above with a compound of the formula IX* shown above or a borane adduct thereof, in both cases starting from a compound of the formula from IVB* (alone or optionally in mixture with a compound of the formula VB*), in the case of mixtures of compounds of the formula IVA* and VA* or IVB* and VB* optionally after isolating the compounds of the formula IVA* or IVB*, respectively, from the undesired enantiomer of the formula VA* or VB*.

7. The process according to claim 6, further comprising reacting the compound of the formula

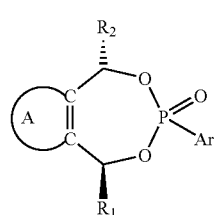

(VIIIA)

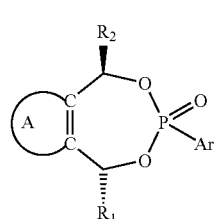

(VIIIB)

wherein ring A, $R_1$ and $R_2$ have the meanings indicated for compounds of the formula IVA and IVB in claim 9 and Ar is aryl, with a phosphine of the formula IX or IX*, $$R_3-PH_2 \quad (IX)$$

$$H_2P-R_3^*-PH_2 \quad (IX^*)$$

(or the corresponding borane adduct thereof) wherein $R_3$ is a monovalent and $R_3^*$ a bivalent organic moiety that can be bound to phosphorus, resulting in a phospholane compound of the formula XA or XA* (from VIIIA); or XB or XB* (from VIIIB) shown in claim 6, respectively.

8. A process for the preparation of a ligand of the formula XIIA or XIIA* shown below from a compound of the formula IVA as defined in claim 1 or of the formula XIIB or XIIB* shown below from a compound of the formula IVB as defined in claim 1, comprising
a) reacting a compound of the formula IVA or IVB with a compound of the formula XI or XI*, $$R_3\text{—}P(L)_2 \qquad (XI)$$

$$(L)_2\text{—}P\text{—}R_3^*\text{—}P\text{-}(L)_2 \qquad (XI^*)$$

wherein $R_3$ is a monovalent and $R_3^*$ a bivalent organic moiety that can be bound to phosphorus and L is a leaving group, leading to ligands of the formula XIIA or XIIA* (from IVA) and/or XIIB or XIIB* (from IVB),

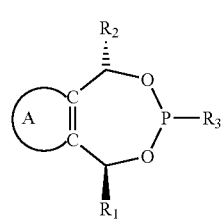
(XIIA)

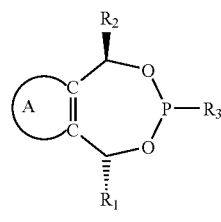
(XIIB)

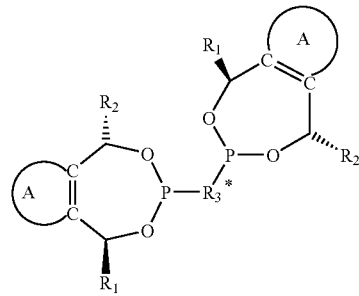
(XIIA*)

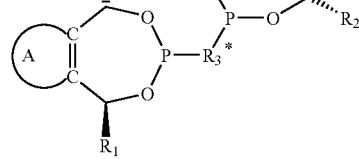
(XIIA*)

wherein ring A, $R_1$ and $R_2$ have the meanings indicated for compounds of the formula IVA and IVB in claim 1 and $R_3$ is a monovalent and $R_3^*$ a bivalent organic moiety that can be bound to phosphorus; or
b) reacting a compound of the formula IVA or IVB with a compound of the formula XI or XI*, $$R_3\text{—}P[N(alk)_2]_2 \qquad (XI^{**})$$

$$[(alk)_2N]_2P\text{—}R_3^*\text{—}P[N(alk)_2]_2 \qquad (XI^{***})$$

wherein $R_3$ is a monovalent and $R_3^*$ a bivalent organic moiety and
alk is alkyl which can be linear or cyclic, or is a heterocyclic radical, with removal of the secondary amine $HN(alk_2)_2$, yielding the compound of formula XIIA or XIIA* (from IVA); or XIIB or XIIB* (from IVB) described above, respectively.

9. A ligand of the formula XIIA, XIIA*, XIIB or XIIB*, as shown in claim 8.

10. A transition metal complex comprising a ligand of the formula XIIA, XIIA*, XIIB or XIIB*, as shown in claim 8.

11. A process for the preparation of a ligand of the formula XIVA from a compound of the formula IVA or of the formula XIVB from a compound of the formula IVB,

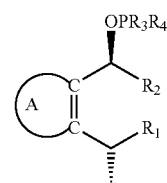
(XIVA)

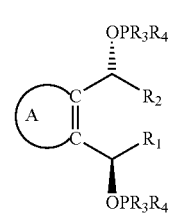
(XIVB)

wherein ring A, $R_1$ and $R_2$ are as defined for compounds of the formula IVA or IVB in claim 1 and $R_3$ and $R_4$ each are, independently of the other, an organic moiety that can be bound to phosphorus,
said process comprising reacting a compound of the formula IVA or VIB given in claim 1, respectively, with
a) a compound of the formula XIII, $$R_3R_4P\text{-}L \qquad (XIII)$$

wherein $R_3$ and $R_4$ are organic moieties that can be bound to phosphorus and L is a leaving group, resulting in a compound of the formula XIVA (from IVA) or XIVB (from IVB), respectively; or
b) with a compound of the formula XIII*, $$R_3R_4PN(alk)_2 \qquad (XIII^*)$$

wherein $R_3$ and $R_4$ are, independently form each other, an organic moiety and alk is alkyl which can be linear or cyclic, or is a heterocyclic radical, with removal of the amine $H_2N(alk)_2$.

12. A ligand of the formula XIVA or XIVB, as shown in claim 11.

13. A transition metal complex comprising a ligand of the formula XIVA or XIVB, as shown in claim 11.

* * * * *